US006395876B1

(12) United States Patent
Munn et al.

(10) Patent No.: US 6,395,876 B1
(45) Date of Patent: May 28, 2002

(54) HIGH-AFFINITY TRYPTOPHAN TRANSPORTER

(75) Inventors: David Munn; Andrew Mellor, both of Augusta, GA (US)

(73) Assignee: Medical College of Georgia Research Institute, Inc., Augusta, GA (US)

( * ) Notice: Subject to any disclaimer, the term of this patent is extended or adjusted under 35 U.S.C. 154(b) by 0 days.

(21) Appl. No.: 09/205,939

(22) Filed: Dec. 4, 1998

Related U.S. Application Data

(60) Provisional application No. 60/067,610, filed on Dec. 5, 1997, provisional application No. 60/080,384, filed on Apr. 1, 1998, and provisional application No. 60/080,380, filed on Apr. 1, 1998.

(51) Int. Cl.$^7$ .................. C07K 14/705; C07K 14/47
(52) U.S. Cl. ................................................ 530/350
(58) Field of Search ........................................ 530/350

(56) References Cited

U.S. PATENT DOCUMENTS

| | | | |
|---|---|---|---|
| 4,244,946 A | 1/1981 | Rivier et al. | 424/177 |
| 4,305,872 A | 12/1981 | Johnston et al. | 260/112.5 R |
| 4,316,891 A | 2/1982 | Guillemin et al. | 424/177 |
| 4,629,784 A | 12/1986 | Stammer | 530/328 |
| 4,792,525 A | 12/1988 | Ruoslahti et al. | 435/240.2 |
| 4,868,116 A | 9/1989 | Morgan et al. | 435/240.2 |
| 4,980,286 A | 12/1990 | Morgan et al. | 435/122.3 |
| 5,244,807 A | 9/1993 | Murtfeldt et al. | |
| 5,723,325 A | 3/1998 | Murtfeldt et al. | |
| 5,874,560 A | * 2/1999 | Kawakami et al. | |

FOREIGN PATENT DOCUMENTS

| | | |
|---|---|---|
| EP | 0 385 385 | 9/1990 |
| WO | WO 93/01286 | 1/1993 |

OTHER PUBLICATIONS

Attwood, "The role of tryptophan depletion in T cell suppression by macrophages," *Immunology* 92(supp. 1):7 (1997).
Aune and Pogue, "Inhibition of tumor cell growth by interferon–gamma is mediated by two distinct mechanisms dependent upon oxygen tension: induction of tryptophan degradation and depletion of intracellular nicotinamide adenine dinucleotide," *J. Clin. Invest.* 84:863–875 (1989).
Blume, et al., "Triple Helix Formation by Purine–rich Oligonucleotides Targeted to the Human Dihydrofolate Reductase Promoter," *Nucl. Acids Res.* 20:1777–1784 (1992).
Burke, et al., "The role of indoleamine 2,3–dioxygenase in the anti–tumour activity of human interferon–gamma in vivo," *Int J Cancer.* 60(1):115–22 (1995).
Carlin, et al., "Interferon–induced indoleamine 2,3–dioxygenase activity in human mononuclear phagocytes," *J Leukoc Biol.* 45(1):29–34 (1989).
Casciari, et al., "Glucose diffusivity in multicellular tumor spheroids," *Cancer Res.* 48:3905–3909 (1988).
Cheng and Prusoff Relationship between the inhibition constant (K1) and the concentration of inhibitor which causes 50 per cent inhibition (I50) of an enzymatic reaction. *Biochem. Pharmacol.* 22: 3099–3108 (1973).
Cooney, et al., "Site–Specific Oligonucleotide Binding Represses Transcription of the Human c–myc Gene in Vitro," *Science* 241: 456–459 (1988).
Crooke, "Progress Toward Oligonucleotide Therapeutics: Pharmacodynamic Properties," *FASEB J.* 7: 533–539 (1993).
Duval–Valentin, et al., "Specific Inhibition of Transcription by Triple Helix–Forming Oligonucleotides," *Proc. Natl. Acad. Sci. USA*, 89: 504–508 (1992).
Fleckner, et al., "Differential regulation of the human, interferon inducible tryptophanyl–tRNA synthetase by various cytokines in cell lines," *Cytokine*7: 70–77 (1995).
Fleckner, et al., "Human interferon gamma potently induces the synthesis of a 55–kDa protein (gamma 2) highly homologous to rabbit peptide chain release factor and bovine tryptophanyl–tRNA synthetase," *Proc Natl Acad Sci U S A*. 88(24):11520–4 (1991).
Grigoriev, et al., "A Triple Helix–forming Oligonucleotide–Intercalator Conjugate Acts as a Transcriptional Repressor via Inhibition of NF KB Binding to Interleukin–2 Receptor α–Regulatory Sequence," *J. Biol. Chem.* 267: 3389–3395 (1992).
Gupta, et al., "Antiparasitic and antiproliferative effects of indoleamine 2,3–dioxygenase enzyme expression in human fibroblasts," *Infect. Immun.* 62: 2277–2284 (1994).
Hogan, et al., *Manipulating the Mouse Embryo: A Laboratory Manual* Cold Spring Harbor Laboratory Pr. (1986).
Holt, et al., "An Oligomer Complementary to c–myc mRNA Inhibits Proliferation of HL–60 Promyelocytic Cells and Induces Differentiation," *Mol. Cell. Biol.* 8: 963–973 (1988).
Itakura, et al., "Synthesis and use of synthetic oligonucleotides," in *Ann. Rev. Biochem.* 53: 323–356 (1984).

(List continued on next page.)

*Primary Examiner*—Michael Pak
(74) *Attorney, Agent, or Firm*—Mueting, Raasch & Gebhardt, P.A.

(57) ABSTRACT

A high affinity and extremely selective tryptophan transport system present in human monocyte-derived macrophages is disclosed. Human monocyte-derived macrophages include two distinct transporters, a high affinity ($K_m=290\pm160$ nM) transporter that is highly specific for tryptophan and a low affinity ($K_m=27\pm4$ $\mu$M) transporter that is less specific for tryptophan, consistent with the known system L. The tryptophan transport system is predominantly (86%) sodium-independent. The high-affinity system is very specific for tryptophan and shows no transport of any other essential amino acids in the tryptophan transport concentration range. This high-affinity system is expressed at very low levels in fresh monocytes, but undergoes a 10–30 fold induction during macrophage differentiation. This high affinity, tryptophan-selective transport system allows macrophages to take up tryptophan efficiently under conditions of very low substrate concentration, such as can occur at sites of inflammation.

7 Claims, 6 Drawing Sheets

OTHER PUBLICATIONS

Kakuda "Na(+)–independent transport (uniport) of amino acids and glucose in mammalian cells," *J Exp Biol.* 196:93–108 (1994).

Kisselev, "Mammalian tryptophanyl–tRNA synthetases," *Biochimie* 75: 1027–103 (1993).

Krause, et al., "Differential screening identifies genetic markers of monocyte to macrophage maturation," *J. Leuk. Biol.* 60: 540–545 (1996).

Lazar, et al., "Transforming Growth Factor :Mutation of Aspartic Acid 47 and Leucine 48 Results in Different Biological Activities," *Molecular and Cellular Biology* 8(3):1247–1252 (1988).

Lewis, et al., "Automated site–directed drug design: the concept of spacer skeletons for primary structure generation," *Proc. R. Soc. Lond.* 236(1283):125–140 (1989).

Lewis, et al., "Automated site–directed drug design: the formation of molecular templates in primary structure generation," *Proc. R. Soc. Lond.* 236(1283):141–162 (1989).

Li, "The glucose distribution in 9L rat brain multicell tumor spheroids and its effect on cell necrosis," *Cancer* 50(10):2066–73 (1982).

Lovell–Badge, in *Teratocarcinomas and embryonic stem cells, a practical approach*, E.J. Robertson, ed. (IRL Press 1987).

Low, et al., "Glucose deprivation and acute cycloheximide treatment stimulate system L amino acid transport in cultured vascular smooth muscle cells," *J Biol Chem* 269(51):32098–103 (1994).

Low, et al., 1993, "Characterization of system L and system y+ amino acid transport activity in cultured vascular smooth muscle cells," *J. Cell. Physiol.* 156: 626–634 (1993).

Maher et al., "Inhibition of DNA binding proteins by oligonucleotide–directed triple helix formation," *Science* 245: 725–730 (1989).

McGivan, "Regulatory and molecular aspects of mammalian amino acid transport," *Biochem J.* 299 ( Pt 2):321–34 (1994).

McKinlay, et al., "Rational Design of Antiviral Agents," *Annual Review of Pharmacology and Toxicology* 29:111–122 (1989).

Merrifield, "Solid–Phase Peptide Synthesis. I. The Synthesis of a Tetrapeptide," *J. Am. Chem. Soc.* 85:2149–2154 (1964).

Mokrzan, et al., "Methylmercury–thiol uptake into cultured brain capillary endothelial cells on amino acid system L," *J. Pharmacol. Exp. Ther.* 272: 1277–1284 (1995).

Mulligan, "The Basic Science of Gene Therapy," *Science* 260: 926–932 (1993).

Munn and Armstrong, "Cytokine regulation of human monocyte differentiation in vitro: the tumor–cytotoxic phenotype induced by macrophage colony–stimulating factor is developmentally regulated by gamma–interferon," *Cancer Res.* 53: 2603–2613 (1993).

Munn and Cheung, "Antibody–dependent antitumor cytotoxicity by human monocytes cultured with recombinant macrophage colony–stimulating factor. Induction of efficient antibody–mediated antitumor cytotoxicity not detected by isotope release assays," *J. Exp. Med.* 170: 511–526 (1989).

Munn, et al., "Selective activation–induced apoptosis of peripheral T cells imposed by macrophages. A potential mechanism of antigen–specific peripheral lymphocyte deletion," *J. Immunol.* 156: 523–532 (1996).

Narang, et al., "Chemical Synthesis of Deoxyoligonucleotides by the Modified Triester Method," in *Methods Enzymol.* 65:610–620 (1980).

Offensperger, et al., "In Vivo inhibition of duck hepatitis B virus replication and gene expression by phosphorothioate modified antisense oligodeoxynucleotides," *EMBO J.* 12(3):1257–1262 (1993).

Orson, et al., "Oligonucleotide inhibition of IL2Rα mRNA transcription by promoter region collinear triplex formation in lymphocytes," *Nucl. Acids Res.* 19: 3435–3441 (1991).

Ozaki, et al., "Induction of indoleamine 2,3–dioxygenase: a mechanism of the antitumor activity of interferon gamma," *Proc. Natl. Acad. Sci. USA* 85, 1242–1246 (1988).

Perry & Davies, *QSAR: Quantitative Structure–Activity Relationships in Drug Design* pp. 189–193 (Alan R. Liss, inc. 1989).

Postel, et al., "Evidence that a triplex–forming oligodeoxyribonucleotide binds to the c–myc promoter in HeLa cells, thereby reducing c–myc mRNA levels," *Proc. Natl. Acad. Sci. USA* 88: 8227–8231 (1991).

Potter et al "Enhancer–dependent expression of human kappa immunoglobulin genes introduced into mouse pre–B lymphocytes by electroporation," *Proc. Natl. Acad. Sci. USA* 81: 7161 (1984).

Prasad, et al., "Relationship between thyroid hormone transport and neutral amino acid transport in JAR human choriocarcinoma cells," *Endocrinol.* 134: 574–581 (1994).

Ripka, "Computers Picture the Perfect Drug," *New Scientist*, 54–57 (Jun. 16, 1988).

Sanchez Del Pino, et al., "Neutral amino acid transport characterization of isolated luminal and abluminal membranes of the blood–brain barrier," *J. Biol. Chem.* 270: 14913–14918 (1995).

Seymour, et al., "Identification and characterization of a novel, high–affinity tryptophan–selective transport system in human macrophages," *Blood* 90(10): 448a (1997).

Suzuki, "Abalone myoglobins evolved from indoleamine dioxygenase: the cDNA–derived amino acid sequence of myoglobin from *Nordotis madaka*," *J. Prot. Chem.* 13: 9–13 (1994).

Suzuki, et al., "Convergent evolution. The gene structure of Sulculus 41 kDa myoglobin is homologous with that of human indoleamine dioxygenase," *Biochem. Biophys. Acta* 1308: 41–48 (1996).

Szostak, "In Vitro genetics," *TIBS* 19:89–93 (1992).

Taylor and Fong "Relationship between interferon–gamma, indoleamine 2,3–dioxygenase, and tryptophan catabolism," *FASEB J.* 5: 2516–2522 (1991).*

Thomas, et al., "IFN–gamma–mediated antimicrobial response. Indoleamine 2,3–dioxygenase–deficient mutant host cells no longer inhibit intracellular Chlamydia spp. or Toxoplasma growth," *J. Immunol.* 150: 5529–5534 (1993).*

Werner, et al., Human macrophages degrade tryptophan upon induction by interferon–gamma. *Life Sci.* 41: 273–280.*

Wickstrom, et al., "Human promyelocytic leukemia HL–60 cell proliferation and c–myc protein expression are inhibited by an antisense pentadecadeoxynucleotide targeted against c–myc mRNA," *Proc. Natl. Acad. Sci. USA* 85: 1028–1032 (1988).*

Young, et al., "Triple helix formation inhibits transcription elongation in vitro," *Proc. Natl. Acad. Sci. USA* 88: 10023–10026 (1991).*

Zamecnik, et al., "Inhibition of *Rous sarcoma* virus replication and cell transformation by a specific oligodeoxynucleotide," *Proc. Natl. Acad. Sci. USA* 75: 280–284 (1978).*

Zamecnik, et al., "Inhibition of replication and expression of human T-cell lymphotropic virus type III in cultured cells by exogenous systhenic oligonucleotides complementary to viral RNA," *Proc. Natl. Acad. Sci.* 83: 4143–4146 (1986).*

Zhu, et al., "Systemic Gene Expression After Intravenous DNA Delivery into Adult Mice," *Science* 261: 209–211 (1993).*

Zimmer and Gruss, Production of chimaeric mice containing embryonic stem (ES) cells carrying a homoeobox Hox 1.1 allele mutated by homologous recombination, *Nature* 338: 150–153 (1989).*

Bliznakov, "Serotonin and its precursors as Modulators of the Immunological Responsiveness in Mice," *J. Med.*, 11(2–3):81–105 (1980).

Cady et al., "1-Methyl-DL-tryptophan, β-(3-Benzofuranyl)-DL-alanine (the Oxygen Analog of Tryptophan), and β-[3-Benzo(b)thienyl]-DL-alanine (the Sulfur Analog of Tryptophan) Are Competitive Inhibitors for Indoleamine 2,3-Dioxygenase$^1$," *Arch. Biochem. Biophys.*, 291:326–333 (1991).

Chapman et al., "Pharmacologically Active Benzo[b]thiophen Derivatives. Part VIII.$^1$ Benzo[b]thiophen Analogues of Tryptophan and α-Methyltryptophan, and Some of their 5-Substituted Derivatives," *J. Chem. Soc.*, (C):1855–1858 (1969).

Hayaishi, "Utilization of Superoxide Anion by Indoleamine Oxygenase-Catalyzed Tryptophan and Indoleamine Oxidation," *Exp. Med. Biol.*, 398:285–289 (1996).

Kamath et al., "Amino Acid-Restricted Diets in the Treatment of Mammary Adenocarcinoma in Mice $^{1,2}$," *J. Nutr.*, 118(9):1137–1142 (1988).

Laske et al., "Investigations on the Antiproliferative Effects of Amino Acid Antagonists Targeting for Aminoacyl-tRNA Synthetases," *Arch. Pharm.*, 322(12):857–862 (1989).

Peterson et al., "Evaluation of Functionalized Tryptophan Derivatives and Related Compounds as Competitive Inhibitors of Indoleamine 2,3-Dioxygenase$^1$," *Med. Chem. Res.*, 3:531–544 (1994).

Schröeder et al., "Suppression of the Modulatory Effects of the Antileukemic and Anti–Human Immunodeficiency Virus Compound Avarol on Gene Expression," *Can. Res.*, 49(8):2069–2076 (1989).

Sidransky et al., "Effect of Tryptophan on Hepatoma and Host Liver of Rats," *Exp. Mol. Pathol.*, 35(1):124–136 (1981).

Southan et al., "Structural requirements of the competitive binding site of recombinant human indoleamine 2,3-dioxygenase," *Med. Chem. Res.*, 6:343–352 (1996).

Takikawa et al., "Mechanism of Interferon-γ Action," *J. Biol. Chem.*, 263:2041–2046 (1988).

Agrawal et al., "Oligodeoxynucleoside phosphoroamidates and phosphorothioates as inhibitors of human immunodeficiency virus", *Proc. Natl. Acad. Sci. USA*, 85:7079–7083 (1988).

Albertati-Giani et al., "Regulation of the Kynurenine Metabolic Pathway by Interferon-γ in Murine Cloned Macrophages and Microglial Cells", *J. Neurochem.*, 66(3):996–1004 (1996).

Albina et al., "Nitric Oxide Production is Required for Murine Resident Peritoneal Macrophages to Suppress Mitogen-Stimulated T Cell Proliferation", *J. Immunol.*, 147(1):144–148 (1991).

Askew et al., "Molecular Recognition with Convergent Functional Groups. 6. Synthetic and Structural Studies with a Model Receptor for Nucleic Acid Components", *J. Am. Chem. Soc.*, 111:1082–1090 (1989).

Azuma et al., "B70 antigen is a second ligand for CTLA-4 and CD28", *Nature*, 366:76–79 (1993).

Baynes et al., "Lactoferrin and the Inflammatory Response", *Adv. Exp. Med. Biol.*, 357:133–141 (1994).

Begg et al., "Delayed Hematopoietic Development in Osteopetrotic (op/op) Mice", *J. Exp. Med.*, 177:237–242 (1993).

Belongia et al., "An Investigation of the Cause of the Eosinophilia–Myalgia Syndrome Associated with Tryptophan Use", *The New England Journal of Medicine*, 323(6):357–365 (1990).

Bock et al., eds., "Polyfunctional Cytokines: IL-6 and LIF", Ciba Foundation Symposium 167, Title page and Table of Contents (1992).

Bock et al., eds., "Interactions Among Cell Signalling Systems", Ciba Foundation Symposium 164, Title page and Table of Contents (1992).

Bogdan, "The Multiplex Function of Nitric Oxide in (Auto)immunity", *J. Exp. Med.*, 187(9):1361–1365 (1998).

Bonney et al., "Much IDO about pregnancy", *Nature Medicine*, 4(10):1128–1129 (1998).

Brás et al., "Nitric Oxide Regulates Clonal Expansion and Activation-Induced Cell Death Triggered by Staphylococcal Enterotoxin B", *Infection and Immunity*, 65(10):4030–4037 (1997).

Capecchi, Ed., "Molecular Genetics of Early Drosophila and Mouse Development", *Current Communications in Molecular Biology*, Cold Spring Harbor Laboratory Press, Title page and Table of Contents (1989).

Cecchini et al., "Role of colony stimulating factor–1 in the establishment and regulation of tissue macrophages during postnatal development of the mouse", *Development*, 120:1357–1372 (1994).

Chen et al., Eradication of Murine Bladder Carcinoma by Intratumor Injection of Bicistronic Adenoviral Vector Carrying cDNAs for the IL–12 Heterodimer and Its Inhibition by the IL–12 p40 Subunit Homodimer, *The Journal of Immunology*, 159:351–359 (1997).

Chon et al., "Cooperative Role of Interferon Regulatory Factor 1 and p91 (STAT1) Response Elements in Interferon-γ-inducible Expression of Human Indoleamine 2,3-Dioxygenase Gene", *J. Biol. Chem.*, 271(29):17247–17252 (1996).

Cicala et al., "NO-naproxen modulates inflammation, nociception and downregulates T cell response in rat Freund's adjuvant arthritis", *British Journal of Pharmacology*, 130(6):1399–1405 (2000).

Dai et al., "Molecular Cloning, Sequencing and Expression of Human Interferon-γ-Inducible Indoleamine 2,3-Dioxygenase cDNA", *Biochemical and Biophysical Research Communications*, 168(1):1–8 (1990).

Dalton et al., "Multiple Defects of Immune Cell Function in Mice with Disrupted Interferon-γGenes", *Science*, 259:1739–1742 (1993).

Däubener et al., "Establishment of T-helper type 1- and T-helper type 2-like human Toxoplasma antigen-specific T-cell clones", *Immunology*, 86:79–84 (1995).

Däubener et al., "Anti–parasitic effector mechanisms in human brain tumor cells: role of interferon–γ and tumor necrosis factor–α", *Eur. J. Immunol*, 26:487–492 (1996).

Dong et al., "Activation of CFTR chloride current by nitric", *EMBO J.*, 14(12): 2700–2707 (1995). Abstract only (1 pg.).

Efron et al., "Nitric oxide generation from L–arginine is required for optimal human peripheral blood lymphocyte DNA synthesis", *Surgery*, 110:327–334 (1991).

Ellington et al., "Selection in vitro of single–stranded DNA molecules that fold into specific ligand–binding structures", *Nature*, 355(6363):850–852 (1992).

Fearon et al., "The Instructive Role of Innate Immunity in the Acquired Immune Response", *Science*, 272:50–54 (1996).

Feng et al., "Interferon γ–resistant mutants are defective in the induction of indoleamine 2,3–dioxygenase", *Proc. Natl. Acad. Sci. USA*, 86:7144–7148 (1989).

Gmünder et al., "Macrophages Regulate Intracellular Glutathione Levels of Lymphocytes. Evidence for an Immunoregulatory Role of Cysteine", *Cell. Immunol.*, 129:32–46 (1990).

Habara–Ohkubo et al., "Cloning and expression of a cDNA encoding mouse indoleamine 2,3–dioxygenase", *Gene*, 105(2):221–227 (1991).

Heesen et al., "$\beta_2$–Adrenoceptor Density of Human Lymphocytes After Nitroprusside–Induced Hypotension", *Anesth Analg*, 81:1250–1254 (1995).

Ibrahim et al., "The injured cell: the role of the dendritic cell system as a sentinel receptor pathway", *Immunology Today*, 16(4):181–186 (1995).

Iwata et al., "Thiol–Mediated Redox Regulation of Lymphocyte Proliferation. Possible Involvement of Adult T Cell Leukemia–Derived Factor and Glutathione in Transferrin Receptor Expression", *J. Immunol.*, 152:5633–5642 (1994).

Janeway, Jr., "The immune system evolved to discriminate infectious nonself from noninfectious self", *Immunology Today*, 13(1):11–16 (1992).

Jorgensen et al., "Gene therapy in osteoarticular diseases: where are we?", *Immunology Today*, 19(9):387–391 (1998).

Kakuda et al., "$Na^+$–Independent Transport (Uniport) of Amino Acids and Glucose in Mammalian Cells", *J. Exp. Biol.*, 196:93–108) 1994).

Kamijo et al., "Mice That Lack the Interferon–γ Receptor Have Profoundly Altered Responses to Infection with Bacillus Calmette–Guérin and Subsequent Challenge with Lipopolysaccharide", *J. Exp. Med.*, 178:1435–1440 (1993).

Kamimura et al., "Localization and Developmental Change of Indoleamine 2,3–Dioxygenase Activity in the Human Placenta", *Acta Med Okayama*, 45(3):135–139 (1991).

Koide et al., "The Signal Transduction Mechanism Responsible for Gamma Interferon–Induced Indoleamine 2,3–Dioxygenase Gene Expression", *Infection and Immunity*, 62(3):948–955 (1994).

Kolb et al., "Nitric oxide in autoimmune disease: cytotoxic or regulatory mediator?", *Immunology Today*, 19(12): 556–561 (1998).

Konan et al., "Importance of the Two Interferon–stimulated Response Element (ISRE) Sequences in the Regulation of the Human Indoleamine 2,3–Dioxygenase Gene", *J. Biol. Chem.*, 271(32):19140–19145 (1996).

Krakowski et al., "Interferon–γ confers resistance to experimental allergic encephalomyelitis", *Eur. J. Immunol.*, 26:1641–1646 (1996).

Lyons, "The Role of Nitric Oxide in Inflammation", *Advances in Immunology*, 60:323–371 (1995).

Mackensen et al., "Delineation of the Dendritic Cell Lineage by Generating Large Numbers of Birbeck Granule–Positive Langerhans Cells from Human Peripheral Blood Progenitor Cells In Vitro", *Blood*, 86(7):2699–2707 (1995).

MacMicking et al., "Nitric Oxide and Macrophage Function", *Annu. Rev. Immunol.*, 15:323–350 (1997).

Mayeno et al., "Characterization of "Peak," a Novel Amino Acid Associated with Eosinophilia–Myalgia Syndrome", *Science*, 250:1707–1708 (1990).

Medawar, "Some Immunological and Endocrinological Problems Raised by the Evolution of Viviparity in Vertebrates", *Symp. Soc. Exp. Biol.*, 7:320–338 (1953).

Mellor et al., "Tryptophan catabolism and T–cell tolerance: immunosuppression by starvation?", *Immunology Today*, 20(10):469–473 (1999).

Mellor et al., "HLA–G transgenic mice", *Journal of Reproductive Immunology*, 43:253–261 (1999).

Mellor et al., Immunology at the Maternal–Fetal Interface: Lessons for T Cell Tolerance and Suppression, *Annu. Rev. Immunol*, 18:367–391 (2000).

Mellor et al., "Prevention of T cell–driven complement activation and inflammation by tryptophan catabolism during pregnancy", *Nature Immunology*, 2(1):64–68 (2001).

Merrifield, "Solid Phase Peptide Synthesis. I. The Synthesis of a Tetrapeptide", *J. Am. Chem. Soc.*, 85:2149–2154 (1963).

Meyer et al., "Trptophan metabolism in chronic inflammatory lung disease", *J. Lab. Clin. Med.*,126(6):530–540 (1995).

Miki et al., Abstract #714, "Indoleamine 2, 3– Dioxygenase Blockade Prevents Spontaneous Liver Allograft Tolergenicity in the Mouse", *Transplantation®*, 69(8):S297 (2000).

Mills, "Molecular Basis of "Suppressor" Macrophages— Arginine Metabolism via the Nitric Oxide Synthetase Pathway", *J. Immunol.*, 146(8):2719–2723 (1991).

Moffett et al., "Antibodies to quinolinic acid and the determination of its cellular distribution within the rat immune system", *Cell Tissue Res.*, 278:461–469 (1994).

Mondino et al., "The anatomy of T–cell activation and tolerance", *Proc. Natl. Acad. Sci. USA*, 93:2245–2252 (1996).

Moore et al., "Enhanced Response of Macrophages to CSF–1 in Autoimmune Mice", *J. Immunol*, 157:433–440 (1996).

Morahan et al., "Macrophage Heterogeneity", *Macrophages and Cancer*, pp. 1–25 (Heppner G.H., Fulton A.M., eds.) CRC Press: Boca Raton, FL (1988).

Morgan et al., "Scleroderma and autoimmune thrombocytopenia associated with ingestion of L–tryptophan", *British Journal fo Dermatology*, 128:581–583 (1993).

Munn, David H., "Regulation of Macrophage Apoptosis," Grant Abstract, Grant No. 1K08HL03395–01 [online]. National Institutes of General Medical Sciences, National Institutes of Health, project dates Jul. 01, 1995–Jun. 30, 1998 [retrieved on Feb. 15, 2001]. Retrieved from the Internet, 2 pages.

Munn, David H., "Inhibition of T Cells by Tryptophan Degradation," Grant Abstract, Grant No. 1R21AI44759–01 [online]. National Institutes of General Medical Sciences, National Institutes of Health, project dates Sep. 30, 1998–Sep. 29, 2000 [retrieved on Feb. 15, 2001]. Retrieved from the Internet: 2 pages.

Munn et al., "Prevention of Allogeneic Fetal Rejection by Tryptophan Catabolism", *Science*, 281:1191–1193 (1998).

Munn et al., "Inhibition of T Cell Proliferation by Macrophage Tryptophan Catabolism", *J. Exp. Med.*, 189(9):1363–1372 (1999).

Munn, David H., "Macrophage Mediated Immunoregulation Via Tryptophan," Grant Abstract, Grant No. 5R01HL60137–03 [online]. National Institutes of General Medical Sciences, National Institutes of Health, project dates Jan. 01, 1999–Dec. 31, 2002 [retrieved on Feb. 15, 2001]. Retrieved from the Internet: URL: http.commons.cit.nih.gov/crisp_lib.getdoc?textkey=6343616&p_query=&ticket= 1890054&p_audit_session_id=3588259&p_keywords=>, 2 pages.

Musso et al., "Interleukin–4 Inhibits Indoleamine 2,3–Dioxygenase Expression in Human Monocytes", *Blood*, 83(5):1408–1411 (1994).

Nagineni et al., "Mechanisms of Interferon–Induced Inhibition of *Toxoplasma gondii* Replication in Human Retinal Pigment Epithelial Cells", *Infection and Immunity*, 64(10):4188–4196 (1996).

Nossal, "Negative Selection of Lymphocytes" *Cell*, 76:229–239 (1994).

Ottaviani et al., "The invertebrate phagocytic immunocyte: clues to a common evolution of immune and neuroendocrine systems", *Immunol. Today*, 18(4):169–174 (1997).

Perry et al., "The Use of 3D Modeling Databases for Identifying Structure—Activity Relationships", QSAR: Quantitative Structure–Activity Relationships in Drug Design, Proceedings of the $7^{th}$ European Symposium on QSAR held in Interlaken, Switzerland, Sep. 5–9, 1988, Alan R. Liss, Inc.—New York, pp. 189–193 (1989).

Pfefferkorn, "Interferon γ blocks the growth of *Toxoplasma gondii* in human fibroblasts by inducing the host cells to degrade tryptophan", *Proc. Natl. Acad. Sci. USA*, 81:908–912 (1984).

Quill, "Anergy as a Mechanism of Peripheral T Cell Tolerance", *J. Immunol.*, 156(4):1325–1327 (1996).

Renault et al., "Base Transitions Are the Most Frequent Genetic Changes at P53 in Gastric Cancer", *Cancer Research*, 53:2614–2617 (1993).

Rosenzwajg et al., Human Dendritic Cell Differentiation Pathway from $CD34^+$ Hematopoietic Precursor Cells, *Blood*, 87(2):535–544 (1996).

Rosoff et al., "4,4'–Diisothiocyanatostilbene–2,2'–disulfonic Acid Inhibits CD3–T Cell Antigen Receptor–stimulated $Ca^{2+}$ Influx in Human T Lymphocytes", *J. Biol. Chem.*, 263(36):19535–19540 (1988).

Rouvinen et al., "Computer–Aided Drug Design", *Acta Pharmaceutica Fennica*, 97:159–166 (1988).

Rubin et al., Interferon Induces Tryptophanyl–tRNA Synthetase Expression in Human Fibroblasts, *The Journal of Biological Chemistry*, 266(36):24245–24248 (1991).

Saadi et al., "Immunology of Xenotransplantation" *Life Sciences*, 62(5):365–387 (1998).

Sambrook et al., *Molecular Cloning: A Laboratory Manual, Second Edition*, Books 1–3, Cold Spring Harbor Laboratory Press, Cold Spring Harbor, New York, Title page and Table of Contents only, 29 pages (1989).

Sardar et al., "Frontal cortex indoleamine–2,3–dioxygenase activity is increased in HIV–1–associated dementia", *Neurosci. Let.*, 187:9–12 (1995).

Sarin et al., "Inhibition of acquired immunodeficiency syndrome virus by oligodeoxynucleoside methylphosphonates", *Proc. Natl. Acad. Sci. USA*, 85:7448–7451 (1988).

Schaller et al., "Identification of the Disulfide Bonds of the Human Complement Component C9 and Comparison with the Other Terminal Compoennts of the Membrane Attack Complex", *MPSA Short Communications*, pp. 472–473 (1996).

Serreze et al., Defects in the Differentiation and Function of Antigen Presenting Cells in NOD/Lt Mice, *J. Immunol.*, 150(6):2534–2543 (1993).

Shaw et al., "Modified deoxyoligonucleotides stable to exonuclease degradation in serum", *Nucleic Acids Res.*, 19(4):747–750 (1991).

Sono et al., "Indoleamine 2,3–Dioxygenase. Equilibrium Studies of the Tryptophan Binding to the Ferric, Ferrous, and Co–Bound Enzymes", *J. Biol. Chem.*, 255(4):1339–1345 (1980).

Springer, "Traffic Signals for Lymphocyte Recirculation and Leukocyte Emigration: The Multistep Paradigm", *Cell*, 76:301–314 (1994).

Steinman, "Escape from "Horror Autotoxicus": Pathogenesis and Treatment of Autoimmune Disease", *Cell*, 80:7–10 (1995).

Sternberg et al., "Development of a Scleroderma–Like Illness During Therapy with L5–Hydroxytryptophan and Carbidopa", *N. Engl. J. Med.*, 303(14):782–787 (1980).

Suzuki, "Abalone Myoglobins Evolved from Indoleamine Dioxygenase: The cDNA–Derived Amino Acid Sequence of Myoglobin from *Nordotis madaka*", *Journal of Protein Chemistry*, 14(1):9–13 (1994).

Szabolcs et al., "Dendritic Cells and Macrophages Can Mature Independently From a Human Bone Marrow-Derived, Post–Colony–Forming Unit Intermediate", *Blood*, 87(11):4520–4530 (1996).

Szostak, "In vitro genetics", *TIBS*, 17(3):89–93 (1992).

Tafuri et al., "T Cell Awareness of Paternal Alloantigens During Pregnancy", *Science*, 270:630–633 (1995).

Takikawa et al., "Mechanism of Interferon–γ Action. Characterization of Indoleamine 2,3–Dioxygenase in Cultured Human Cells Induced by Interferon–γ and Evaluation of the Enzyme–Mediated Tryptophan Degradation in its Anticellular Activity", *The Journal of Biological Chemistry*, 263(4):2041–2048 (1988).

Takikawa et al., "Induction of Indoleamine 2,3–Dioxygenase in Tumor Cells Implanted Into Allogeneic Mouse: Interferon–γ is the Inducer", *Kynurenine and Serotonin Pathways*, pp. 437–444, Plenum Press: New York (1991).

Tarazona et al., "Effects of different antigenic microenvironments on the course of $CD8^+$ T cell responses in vivo", *Intl. Immunol.*, 8(3):351–358 (1996).

Taylor et al., "Relationship between interferon–gamma, indoleamine 2,3–dioxygenase, and tryptophan catabolism", *FASEB J.*, 5:2516–2522 (1991).

Thomas et al., "Nitric Oxide Inhibits Indoleamine 2,3–Dioxygense Activity in Interferon–γ Primed Mononuclear Phagocytes", *J. Biol. Chem.*, 269(20):14457–14464 (1994).

Thomas et al., "Dendritic Cells: Origin and Differentiation", *Stem Cells*, 14:196–206 (1996).

Thomas et al., "Are dendritic cells the key to liver transplant tolerance?", *Immunology Today*, 6 pgs. (1999).

Torre et al., "Immunological Aspects of Nitric Oxide in HIV–1 Infection", *Medical Hypotheses*, 47:405–407 (1996).

Trinchieri et al., "Immunoregulation by interleukin–12", *J. Leukocyte Biol.*, 59:505–511 (1996).

Unanue et al., The Basis for the Immunoregulatory Role of Macrophages and Other Accessory Cells, *Science*, 236:551–557 (1987).

Venkateshan et al., "Immunocytochemical localization of the endogenous neuroexcitotoxin quinolinate in human peripheral blood monocytes/macrophages and the effect of human T–cell lymphotropic virus type I infection", *Proc. Natl. Acad. Sci. USA*, 93:1636–1641 (1996).

Vogelgesang et al., "Quinolinic Acid in Patients with Systemic Lupus Erythematosus and Neuropsychiatric Manifestations", *J. Rheumatol*, 23(5):850–855 (1996).

Weiss et al., "Linkage of cell–mediated immunity to iron metabolism", *Immunology Today*, 16(10):495–500 (1995).

Willenborg et al., IFN–γ Plays a Critical Down–Regulatory Role in the Induction and Effector Phase of Myelin Oligodendrocyte Glycoprotein–Induced Autoimmune Encephalomyelitis, *J. Immunol*, 157:3223–3227 (1996).

Yu et al., "Moleclar mechanisms underlying IFN–γ–mediated tumor growth inhibition induced during tumor immunotherapy with rIL–12", *Int. Immunol*, 8(6):855–865 (1996).

Zhou et al., "Expanded cohorts of maternal CD8$^+$ T–cells specific for paternal MHC class I accumlate during pregnancy", *J. Reprod. Immunol.*, 40:47–62 (1998).

Zhou et al., "Evidence for a Close Link between the Thyroid Hormone Transport System and the Aromatic Amino Acid Transport System T in Erythrocytes", *J. Biol. Chem.*, 265(28):17000–17004 (1990).

Janeway, Jr. et al., *ImmunoBiology, The Immune System in Health and Disease*, Current Biology Limited, London, U.K., 12:30–12:34 (1994).*

* cited by examiner

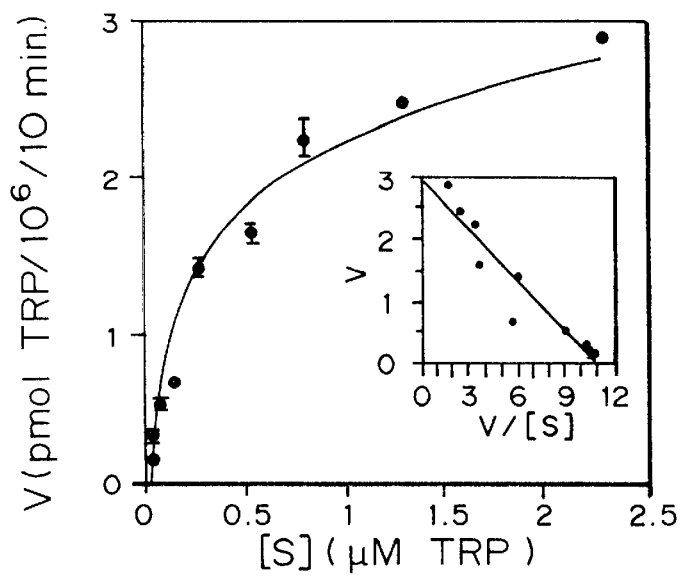
FIG. 1A
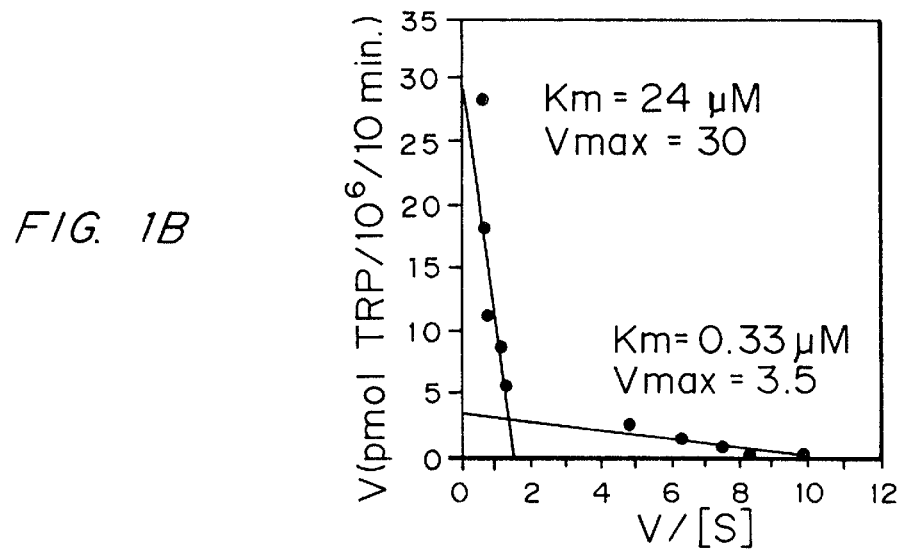
FIG. 1B
FIG. 1C
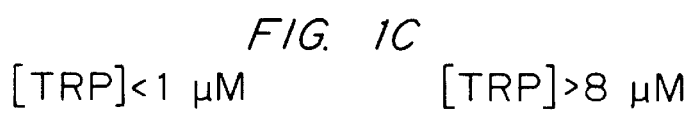
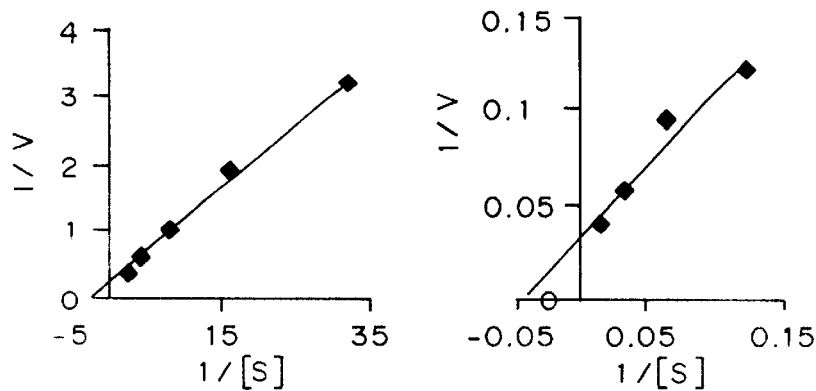

HIGH-AFFINITY TRYPTOPHAN TRANSPORTER

This application claims priority to U.S. Serial No. 60/067,610 entitled "Regulation of T Cell Activation" filed Dec. 5, 1997; U.S. Serial No. 60/080,384 entitled "Regulation of Pregnancy" filed Apr. 1, 1998; and U.S. Serial No. 60/080,380 entitled "IDO Inhibitors for Use as Antiviral Agents" filed Apr. 1, 1998, by David Munn and Andrew Mellor.

The United States government has rights in this invention by virtue of grant K08 HL3395 from the National Institutes of Health.

BACKGROUND OF THE INVENTION

This invention is generally in the field of tryptophan transporters, and more specifically is drawn to a novel tryptophan transport system.

Tryptophan occupies a unique position at the interface between the immune system and cellular metabolism. It is the only amino acid whose level is specifically and selectively modified in response to signals of infection and inflammation. This is accomplished by the enzyme indoleamine 2,3-dioxygenase (IDO), which rapidly and selectively degrades tryptophan following induction by interferon-$\gamma$ (IFN$\gamma$) and other proinflammatory signals (Taylor and Feng, 1991 *FASEB J.* 5, 2516–2522). The IDO system, whose origins extend back to invertebrates (Suzuki, et al., 1996 *Biochem. Biophys. Acta* 1308, 41–48; Suzuki, 1994 *J. Prot. Chem.* 14, 9–13) is hypothesized to inhibit the replication of intracellular pathogens (Gupta, et al., 1994 *Infect. Immun.* 62, 2277–2284; Thomas, et al., 1993 *J. Immunol.* 150, 5529–5534) and to participate in the antiproliferative effect of interferons on host cells (Aune and Pogue, 1989 *J. Clin. Invest.* 84, 863–875; Feng and Taylor 1989, *Proc. Natl. Acad. Sci. USA*, 86, 7144–7148; Ozaki, et al., 1988, *Proc. Natl. Acad Sci. USA* 85, 1242–1246). Tryptophan is also unique in that it is the only amino acid whose entry into the protein synthetic pathway is regulated by the immune system. Like IDO, the gene for tryptophanyl-tRNA synthetase is highly induced by IFN$\gamma$ (Fleckner, et al., 1991 *Proc. Natl. Acad. Sci. USA* 88, 11520–11524; Fleckner, et al., 1995 *Cytokine* 7, 70–77; Rubin, et al., 1991 *J. Biol. Chem.* 266, 24245–24248), which has been proposed to assist cells in competing for scarce supplies of tryptophan (Kisselev, 1993 *Biochimie* 75, 1027–1039). These observations indicate that tryptophan metabolism plays an important role in host defense.

Activated macrophages display a marked induction of the tryptophan catabolic pathway (Werner, et al., 1987 *Life Sci.* 41, 273–280; Carlin, et al., 1989, *J. Leuk. Biol.* 45, 29–34). These cells are capable of reducing the tryptophan concentration in their local microenvironment to such a low level that cellular proliferation becomes impossible. This mechanism underlies the ability of certain types of macrophages (Munn, et al., 1996 *J. Immunol.* 156, 523–532) to inhibit T cell activation. In order to achieve this effect, however, macrophages must reduce the tryptophan concentration to the low nanomolar range (less than 50 nM), three orders of magnitude below its normal level. Macrophages can continue to take up tryptophan efficiently at very low substrate concentrations, even when tryptophan is competing with multiple other amino acids, present at much higher concentrations, for transport into the cell.

Based on this analysis, it is postulated that there must be a specific, high affinity tryptophan transporter.

It is therefore an object of the present invention to provide a high-affinity amino acid transport system that is highly specific for tryptophan.

It is another object of the present description to provide methods and reagents for use in isolating and characterizing the cDNA and amino acid sequence of high affinity tryptophan transporters.

It is yet a still further object of the present invention to provide methods and reagents for designing and isolating molecules and drugs that can stimulate or inhibit the binding or transport of tryptophan with high affinity tryptophan transporters.

SUMMARY OF THE DISCLOSURE

A high affinity and extremely selective tryptophan transport system present in human monocyte-derived macrophages is disclosed. Human monocyte-derived macrophages include two distinct transporters, a high affinity (Km=290±160 nM) transporter that is highly specific for tryptophan and a low affinity (Km=27±4 $\mu$M) transporter that is less specific for tryptophan, consistent with the known system L. The tryptophan transport system is predominantly (86%) sodium-independent. The high-affinity system is very specific for tryptophan and shows no transport of any other essential amino acids in the tryptophan transport concentration range. This high-affinity system is expressed at very low levels in fresh monocytes, but undergoes a 10–30 fold induction during macrophage differentiation. This high affinity, tryptophan-selective transport system allows macrophages to take up tryptophan efficiently under conditions of very low substrate concentration, such as can occur at sites of inflammation.

Methods for the isolation of the cDNA that codes for this high affinity tryptophan transport system are described along with methods for the purification of the high affinity transporter. Methods for obtaining and using molecules which interact with the high affinity transporter are also described. Molecules which are obtained by their competitive binding properties with tryptophan for the high affinity transporter tryptophan binding site are also described. Also described are compositions, and methods for using these compositions, which do not competitively interact with tryptophan for the high affinity transporter tryptophan binding site.

BRIEF DESCRIPTION OF THE DRAWINGS

FIGS. 1a–c show saturation kinetics for uptake low substrate concentrations (less than 2.5 $\mu$M) of tryptophan transport for the high affinity transporter.

FIG. 1A is a graph of the [v] (pmol Tryptophan/$10^6$/10 minutes) versus [S] ($\mu$M Tryptophan). Monocyte-derived macrophages were incubated with varying concentrations between 0 and 2.5 $\mu$M of radiolabeled tryptophan, and substrate uptake over 10 min (V, expressed in pmol tryptophan $10^6$ cells$^{-1}$ 10 min$^{-1}$) measured as a function of substrate concentration ([S], in $\mu$M). The inset is an Eadie-Hofstee plot of the uptake data, yielding a calculated Km of 230 nM in this experiment. The Km values are described in Table 1.

FIG. 1B is a graph of the [v] (pmol Tryptophan/$10^6$/10 minutes) versus v/[S]. The data was derived from an extended titration of tryptophan over a three log range (32 nM to 64 $\mu$M), demonstrating the presence of two transport systems with markedly different affinities (all data taken from a single experiment using the same macrophage preparation). The superimposed lines represent predicted uptake at concentrations of less than 1 $\mu$M and greater than 8 $\mu$M, based on the Km and Vmax values derived from the Lineweaver-Burk plots shown in FIG. 1C.

FIG. 1C is a Lineweaver-Burk plot for the high affinity data and the low affinity data shown in FIG. 1B, demonstrating that each system followed Michaelis-Menten kinetics over the range of concentrations surrounding its Km value.

(FIG. 9A) day 0 (mean Vmax 0.16±0.15 pmol $10^6$ cells$^{-1}$ 10 min$^{-1}$, n=4 vs. (FIG. 9B) day 4–7 (mean Vmax 2.3±0.9, n=6).

DETAILED DESCRIPTION OF THE DISCLOSURE

Tryptophan Transport Systems in Macrophages

Figure 2A:
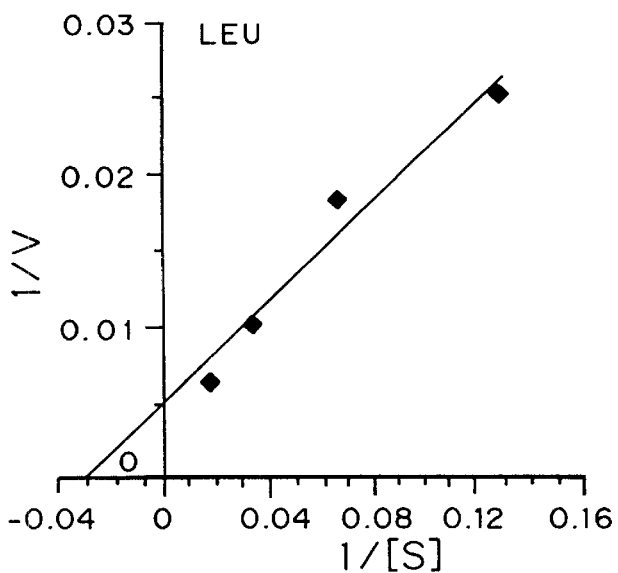
FIGS. 2A and 2B are graphs of 1/v (pmol amino acid $10^6$ cells$^{-1}$ 10 min$^{-1}$) versus 1/[S] ($\mu$M) for tryptophan transport of leucine and phenylalanine via the low affinity transport system. The affinity constants for uptake of radiolabeled (FIG. 2A) leucine (26±6 $\mu$M) and (FIG. 2B) phenylalanine (29±2 $\mu$M) were determined by saturation kinetics as described in FIG. 1.

The known sodium-independent systems are summarized in Kakuda et al., *J. Exp. Biol.* 1994; 196:93–108; McGivan et al., *Biochem. J.* 1994; 299:321–334. There is an IFN$\gamma$-inducible, high-affinity, tryptophan-selective uptake system in MCSF-derived macrophages. A common feature of both sodium-dependent and sodium-independent systems identified to date is that they all display a relatively modest affinity for substrate (Km of even the "high-affinity") systems in the range of 10–30 $\mu$M, and of the low-affinity systems 100–500 $\mu$M). This affinity is consistent with the fact that amino acids are normally found in vivo in this concentration range. Indeed, given the normal physiologic levels of tryptophan (50 $\mu$M), even the possibility of an amino acid transport system with nanomolar affinity seems paradoxical, since it would presumably always exist in a saturated state. However, the local concentration of a substance in tissues may be markedly different from its concentration in the circulation, due to the limited rate of diffusion through the extracellular space (Casciari, et al., 1988 *Cancer Res.* 48, 3905–3909). Data from multicellular spheroid models show that the distance over which even small molecules can be supplied by diffusion in the face of ongoing consumption is limited to 100–200 micrometers (Li 1982 *Cancer* 50, 2066–2073). Thus, local concentrations of tryptophan in tissues could be much lower than those in plasma if the rate of consumption is high enough to exceed delivery. This has been verified empirically in vivo by Burke, et al. 1995 *Int. J. Cancer* 60, 115–122. Consumption of tryptophan by activated macrophages can be very high. As a part of their role in host defense, macrophages possess the inducible enzyme, indoleamine 2,3-dioxygenase (IDO), which rapidly and selectively degrades tryptophan in response to infection and inflammation (Taylor and Feng 1991 *FASEB J.* 5, 2516–2522). Activated macrophages degrade tryptophan via IDO at a rate which is 100 times their already high rate of tryptophan consumption by cellular metabolism. Thus, it is readily conceivable that tryptophan degradation could outstrip diffusion-limited substrate delivery in tissues, resulting in very low local tryptophan concentrations within the immediate microenvironment of the macrophage.

A second feature of most amino acid transporters is that they typically accept multiple amino acids. However, there also exist a small number of selective transport systems, which display relative specificity for a particular amino acid. These systems generally target amino acids with a special biologic role, e.g., glutamate transport in neurons, or tyrosine transport in melanosomes. In these specialized settings, the local concentration of the amino acid of interest may be low, and it must compete for uptake with other amino acids present in higher concentration. In this context, a selective system for a particular amino acid would be advantageous.

The data in FIGS. 1a,b,c indicates that tryptophan transport in macrophages is achieved through two separate transporters. Uptake kinetics performed at the substrate concentrations of interest (sub-micromolar) revealed a saturable system with extremely high affinity for tryptophan. (FIG. 1A) Studies over a more extended range of concentrations revealed that uptake did not follow simple Michaelis-Menton kinetics, but appeared to be due to the presence of two separate transport activities. (FIGS. 1B and 1C).

One system displayed a Km value in the range of 20–30 micromolar and a pattern of substrate specificity consistent with system L (FIG. 1B).

Characterization of the High Affinity Transporter

Figure 3:
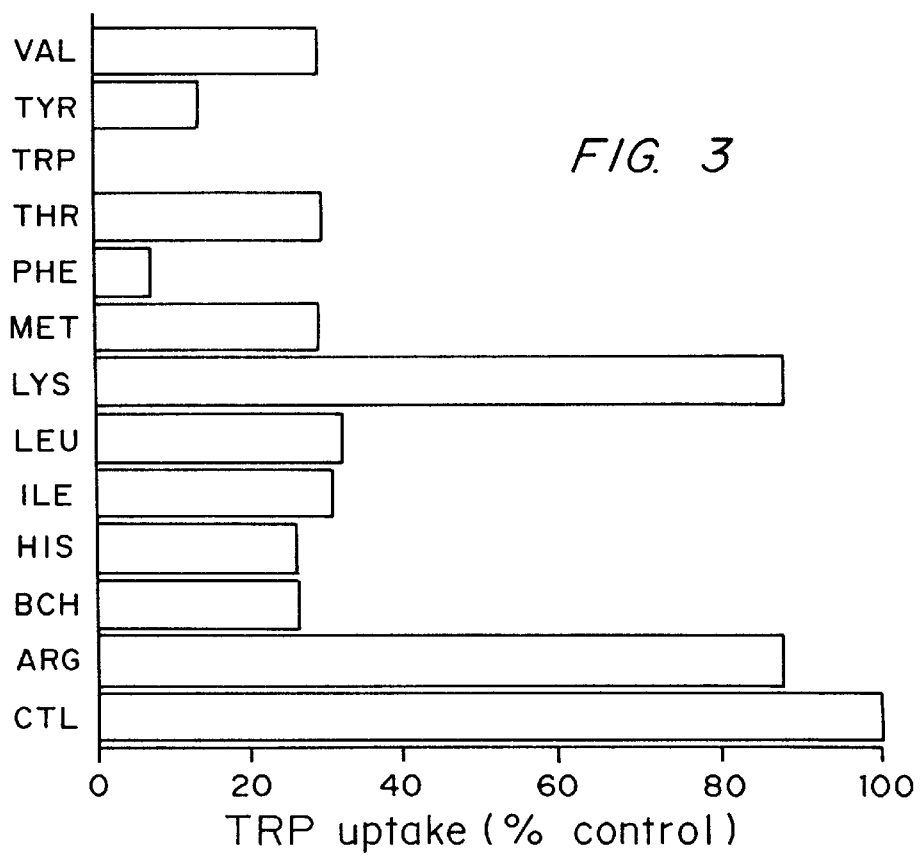
FIG. 3 is a bar graph of the amount of uptake of different amino acids based on the % of tryptophan uptake. Cross-competition studies were performed using radiolabeled tryptophan (125 nM) versus a panel of unlabeled substrates (8 mM each). All data are expressed as tryptophan uptake relative to controls without added competitor ("CTL").
Figure 4A:
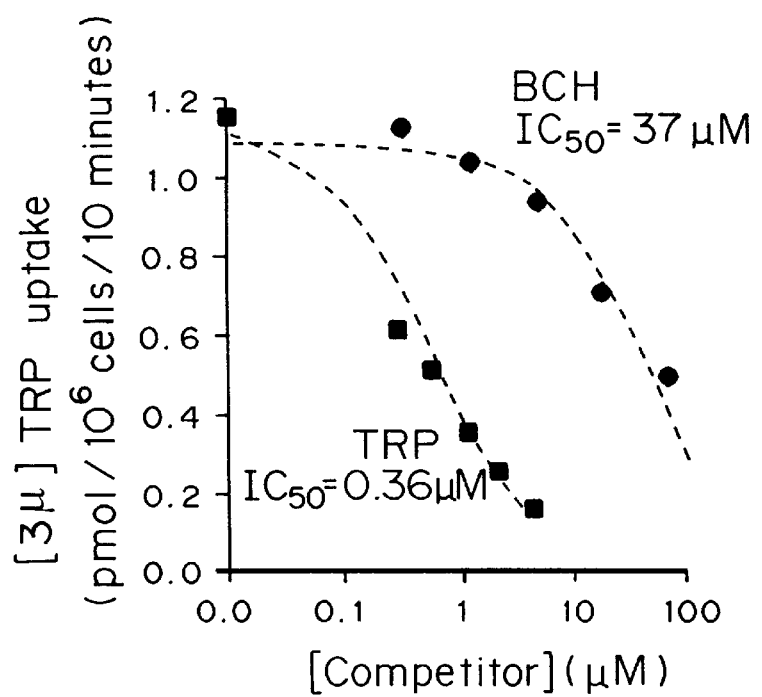
FIG. 4A is a graph of [$^3$H]Tryptophan (pmol Tryptophan/$10^6$/10 minutes) versus [S] ($\mu$M Tryptophan) plotted on a semilog plot. Unlabeled 2-aminobicyclo(2,2,1)-hepatane-2-carboxylic acid (BCH) (diamonds) or tryptophan (squares) were allowed to compete for uptake with radiolabeled tryptophan (125 nM). The dotted lines show the predicted inhibition curves calculated from Equation 1 for single isolated systems, based on the observed $IC_{50}$ values in experiments of 360 nM and 37 $\mu$M for tryptophan and BCH, respectively.
Figure 4B:
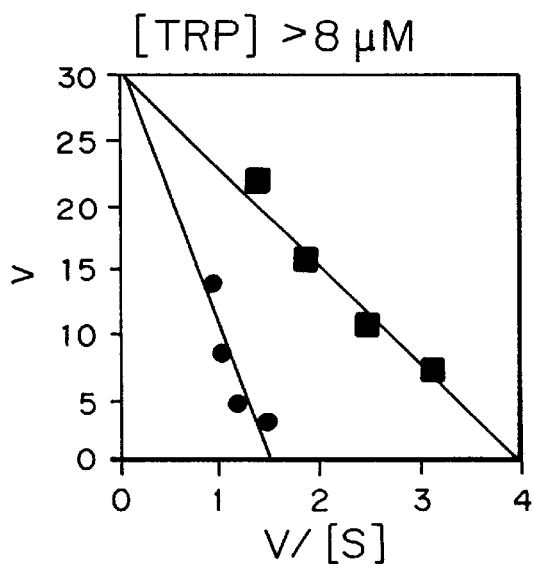
FIGS. 4B and 4C are graphs of V versus. V/[S] at a Tryptophan concentration of greater than 8 $\mu$M (FIG. 5B) and less than 1 $\mu$M (FIG. 4C). Saturation kinetics for tryptophan uptake were performed as described with reference to FIG. 1, in the presence (circles) or absence (squares) of 500 $\mu$M unlabeled BCH. In the concentration range where system L predominated (greater than 8 $\mu$M tryptophan) BCH acted as a competitive inhibitor. However, in the range where the high-affinity system predominated (less than 1 $\mu$M), BCH acted only as a weak non-competitive inhibitor.
Figure 4C:
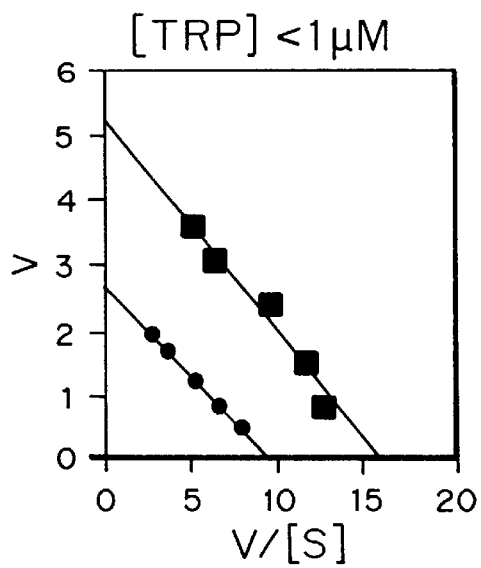

The other tryptophan transporter is a high affinity transport activity with a Km value in the nanomolar range of about 130 nM to about 400 nM (preferably 290 to 340 nM, n=18 experiments with 4 donors), which does not correspond to any known tryptophan transporter (FIG. 1C and Table 1). The data shown in FIGS. 3 and 5 indicate that the transport of tryptophan into macrophages is not completely inhibited by the addition of very high concentrations of similar amino acids. Therefore, macrophages must contain a transporter specific for tryptophan. The data in FIGS. 4a,b,c confirm that there are two separate transporters for tryptophan present in macrophages. The low affinity transporter is a non-specific transporter of amino acids because BCH competitively inhibits tryptophan transport (FIG. 4B). This type of transport is similar to system L. The high affinity system is specific for tryptophan because BCH is not able to compete for transport at concentrations below which the low affinity transporter can function (FIG. 4C).

The high affinity transporter is very specific for tryptophan transport. Other amino acids, including neutral amino acids, do not compete with tryptophan for transport into macrophages, by the high affinity system. The data shown in FIG. 6 indicate that unlabeled competitor amino acids, selected from the group of VAL, TYR, THR, PHE, MET, LYS, LEU, ILE, HIS, BCH, and ARG, used at 4 micromolar, which should significantly inhibit a system with nanomolar affinity, have little impact on the high affinity transporter in transporting tryptophan. System L with a Km approximately 30 micromolar for both the competitor amino acids and tryptophan is not affected at 4 µM competitor. The uptake of radiolabeled tryptophan 125 nM) was markedly inhibited by 4 micromolar cold tryptophan indicating that a 4 µM ligand is sufficient to compete with the radiolabeled ligand as long as the transporter is capable of binding the ligand. In contrast, 4 µM of any of the tested amino acids (including BCH) was unable to out compete the tryptophan transport.

The 5-hydroxy derivative of tryptophan, which differs from native tryptophan only in a single substitution on the side chain, similarly failed to compete for transport via the high-affinity system (FIG. 7), indicating the exquisite specificity of the high-affinity system for tryptophan. Some amino acids showed non-competitive inhibition of the high-affinity system at high concentrations. However, even at millimolar concentrations 20,000 times greater than the Km of the high-affinity system, no competing amino acid except tryptophan itself could fully inhibit uptake of labeled tryptophan.

Figure 8:
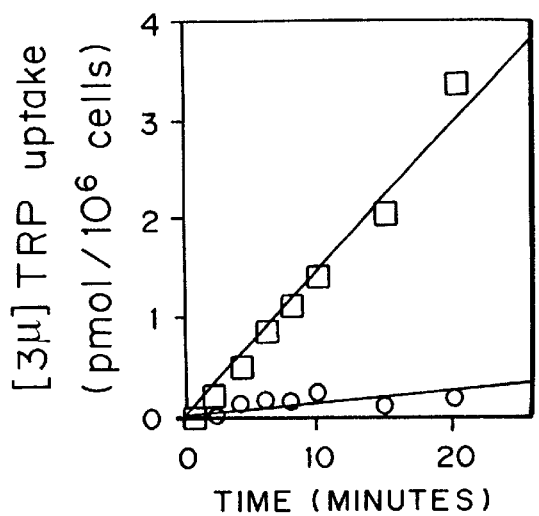
FIG. 8 is a graph of tryptophan uptake inhibition at 25° C. (squares) and 0° C. (circles), one of three experiments.

The data shown in FIG. 8 indicates that the higher association of tryptophan, relative to other amino acids, with macrophages is caused by increased relative transport at low concentrations, not simple binding to the macrophage surface. If the observed results are due to simple binding, a reduction in temperature should slow the rate of binding, but the reaction should come to equilibrium. The data in FIG. 8 indicate that the amount of tryptophan associated with the macrophages is decreased and it is not in equilibrium, indicating a reduced rate of influx. The Vmax of tryptophan transport by the high affinity transporter, normalized by the number of cells, increases when peripheral blood monocytes are induced to differentiate by growth in the presence of macrophage colony stimulating factor (MCSF) FIGS. 9a,b, c). This increase in velocity is likely caused by an upregulation of the expression of the high affinity tryptophan transporter in macrophages, relative to the progenitor peripheral blood cells.

The high affinity transporter represents an excellent target for the inhibition or activation of tryptophan transport. Tryptophan uptake in macrophages represents a special case in which both high affinity and high selectivity are necessary. At nanomolar substrate concentrations, tryptophan uptake via system L would become inefficient, and it would be rendered even less efficient by the fact that multiple other substrates would compete for uptake. When Equation 1 is used to predict the uptake of low concentrations of tryptophan via system L alone (50 nM tryptophan, 1 mM total other competing amino acids, and Km and Vmax values as in FIG. 1) uptake is calculated to be 1.5 fmol $10^6$ cells$^{-1}$ 10 min$^{-1}$. The presence of a selective high-affinity system as described herein would increase tryptophan transport greater than 100-fold, to 70 fmol $10^6$ cells$^{-1}$ 10 min$^{-1}$. It is postulated that macrophages represent a specialized cell type which due to their own high IDO activity must be prepared to function in settings where the local tryptophan concentration is extremely low. A selective, high-affinity transport system would allow macrophages to continue to take up tryptophan efficiently, even under conditions where other cell types could not. Such a transporter could play an important role in supplying substrate to the IDO enzyme system for degradation, and also in allowing macrophages to compete with other cells for available tryptophan.

One significant feature of the transport system is its selective upregulation during macrophage differentiation. Unlike system L, which is constitutively present in fresh monocytes and only modestly increased in mature macrophages (approximately proportional to the increase in cell size), the high-affinity system undergoes 10- to 30-fold upregulation over the same period. This differentiation step from monocyte to macrophages is also known to produce massive increases in both IFNγ-inducible IDO activity (Carlin, et al., 1989 J. Leuk. Biol. 45, 29–34) and IFNγ-inducible tryptophanyl-tRNA synthetase activity (Krause, et al., 1996 J. Leuk. Biol. 60, 540–545). Thus, the high-affinity tryptophan transporter is coordinately regulated during macrophage differentiation with two other genes known to be involved in immunoregulated tryptophan metabolism, indicating that the transporter participates in the tryptophan-mediated Mφ immune response.

The following examples examine expression of the high-affinity transporter in macrophages, where it was first identified. However, it is expected to be present in other cell types which may also have specialized needs for tryptophan transport, such as cells of the nervous system, placenta, or blood-brain barrier.

Isolation of the High Affinity Transporter

The transporter can be isolated using standard techniques, based on the presence relative to the cell walls of the macrophages. Examples of techniques that can be used include differential display and macrophage expression libraries which are screened based on the high affinity and selectivity for tryptophan binding, as described in the examples, then purified using traditional chromatography, membrane fractionation, or other standard techniques. Alternatively, the gene encoding the transporter can be cloned as described below, and the gene (or cDNA) expressed to produce a recombinant protein.

Cloning of the High Affinity Transporter

The unusual features of the transporter can be used to clone the transporter. The transporter is unique in its extremely high affinity for tryptophan, and its selectivity for tryptophan over other amino acids. The previously identified amino acid transporters which accept tryptophan all have affinities in the micromolar-to-milimolar range, and all accept other amino acids which compete with tryptophan for uptake. Thus, under conditions in which the tryptophan concentration is very low (<100 nM) and the total concentration of competing amino acids is very high (greater than 1 mM), cells without the high-affinity transporter would be unable to take up tryptophan efficiently and could not proliferate. However, under these same conditions cells with a high-affinity, tryptophan-selective transporter would still be able to take up tryptophan. Thus, the high-affinity transporter would confer a proliferative advantage under the conditions described.

Applications for the High Affinity Transporter with the Cloned or Purified Transporter The transporter, or gene, can be used to isolate other transporter proteins, to screen for inhibitors of the transporter, which are useful in altering tryptophan transport or T cell activation, and in screening of patient samples for defects in the transporter, which may be indicative of genetic defects, viral or parasitic infections, or malignancy. The transporter protein is also be useful for making antibodies which can be used in diagnostic assays to measure efficacy of tryptophan transport and the effect of compounds on the transporter, as well as isolation of the transporter.

Screening for Compounds which Modulate Tryptophan Transport Via the High Affinity Transporter There are three basic mechanisms which can be used to modulate tryptophan catabolism in cells: modulation of IDO concentration or activity; modulation of the high affinity tryptophan transporter; and modulation of tryptophan concentration in the relevant cellular environment. A number of techniques are known for obtaining compounds which can be used to modulate IDO expression or activity, tryptophan levels, or the activity or expression of the high affinity tryptophan transporter, which in turn regulates the tryptophan levels intracellularly.

Assays for testing compounds for useful activity can be based solely on interaction with IDO, the high affinity tryptophan transporter, or enzymes involved in tryptophan metabolism ("the enzymes"), or alternatively, the assays can be based on interaction with the gene sequence encoding the enzymes. For example, antisense which binds to the regulatory sequences, and/or to the protein encoding sequences can be synthesized using standard oligonucleotide synthetic chemistry. The antisense can be stabilized for pharmaceutical use using standard methodology (encapsulation in a liposome or microsphere; introduction of modified nucleotides that are resistant to degradation or groups which increase resistance to endonucleases, such as phosphorothioates and methylation), then screened initially for alteration of enzyme activity in transfected or naturally occurring cells which express the enzyme, then in vivo in laboratory animals. Typically, the antisense would inhibit expression. However, sequences which block those sequences which "turn off" synthesis can also be targeted.

Random Generation of Enzyme or Enzyme Encoding Sequence Binding Molecules

Oligonucleotide molecules with a given function, catalytic or ligand-binding, can be selected from a complex mixture of random oligonucleotides in what has been referred to as "in vitro genetics" (Szostak, *TIBS* 17:89–93, 1992). One synthesizes a large pool of molecules bearing random and defined sequences and subjects that complex mixture, for example, approximately $10^{15}$ individual sequences in 100 µg of a 100 nucleotide RNA, to some selection and enrichment process. For example, by repeated cycles of affinity chromatography and PCR amplification of the molecules bound to the ligand on the column, Ellington and Szostak (1992) estimated that 1 in $10^{10}$ RNA molecules folded in such a way as to bind a given ligand. DNA molecules with such ligand-binding behavior have been isolated (Ellington and Szostak, 1992; Bock et al., 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules.

Using methodology well known to those of skill in the art, in combination with various combinatorial libraries, one can isolate and characterize those compounds which bind to or interact with the desired target. The relative binding affinity of these compounds can be compared and optimum compounds identified using competitive binding studies which are well known to those of skill in the art.

Screening molecules similar to tryptophan for inhibition of tryptophan binding or transport is a method of isolating desired compounds. The high affinity tryptophan transporter is highly specific for tryptophan transport.

Molecules isolated which inhibit tryptophan transport can either be competitive inhibitors of the high affinity tryptophan transporter or non-competitive inhibitors. In one embodiment the molecules are competitive inhibitors of tryptophan transport by the high affinity transporter. It is preferred that competitive inhibitors of tryptophan transport via the high affinity transporter do not get transported via the low affinity transporter. It is most preferred that competitive inhibitors of tryptophan transport via the high affinity transport system do not get transported via either the high affinity or low affinity transporters. This prevents unwanted intracellular buildup of tryptophan analogs.

In another embodiment the inhibitors of tryptophan transport by the high affinity transporter are non-competitive inhibitors of tryptophan transport. One type of non-competitive inhibitor will cause allosteric rearrangements which prevent the transporter from binding or transporting tryptophan. Another type of non-competitive inhibitor of tryptophan transport by the high affinity transporter binds the high affinity transporter in a place other than the tryptophan binding site. However, it prevents tryptophan from accessing the tryptophan binding site because of stearic hinderance.

Non-competitive inhibitors specific for the high affinity tryptophan transporter are preferred.

Computer Assisted Drug Design

Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modelling systems are the CHARMm and QUANTA programs, Polygen Corporation, Waltham, Mass. CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rouvinen et al., 1988 Acta Pharmaceutica Fennica 97, 159–166; Ripka, *New Scientist* 54–57 (Jun. 16, 1988); McKinlay and Rossmann, 1989 *Annu. Rev. Pharmacol. Toxicol.* 29, 111–122; Perry and Davies, QSAR: Qantitative Structure-Activity Relationships in Drug Design Proceedings of the 7t European Symposium on QSAR held in Interlaken, Switzerland, Sep. 5–9, 1988, pp. 189–193 (Alan R. Liss, Inc. 1989); Lewis and Dean, 1989 *Proc. R. Soc. Lond.* 236, 125–140 and 141–162; and, with respect to a model enzyme for nucleic acid components, Askew, et al., 1989 *J. Am. Chem. Soc.* 111, 1082–1090. Other computer programs that screen and graphically depict chemicals are available from companies such as BioDesign, Inc., Pasadena, Calif., Allelix, Inc., Mississauga, Ontario, Canada, and Hypercube, Inc., Cambridge, Ontario, Canada. Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

Generation of Nucleic Acid Regulators

Nucleic acid molecules containing the 5' regulatory sequences of the enzyme or transporter genes can be used to regulate or inhibit gene expression in vivo. Vectors, including both plasmid and eukaryotic viral vectors, may be used to express a particular recombinant 5' flanking region-gene construct in cells depending on the preference and judgment of the skilled practitioner (see, e.g., Sambrook et al., Chapter 16). Furthermore, a number of viral and nonviral vectors are being developed that enable the introduction of nucleic acid sequences in vivo (see, e.g., Mulligan, 1993 *Science,* 260, 926–932; U.S. Pat. Nos. 4,980,286; 4,868,116; incorporated herein by reference). Nucleic acid can be encapsulated in cationic liposomes which can be injected intravenously into a mammal. This system has been used to introduce DNA into the cells of multiple tissues of adult mice, including endothelium and bone marrow (see, e.g., Zhu et al., 1993 *Science* 261, 209–211).

The 5' flanking sequences of the enzyme gene can also be used to inhibit the expression of the enzyme. For example, an antisense RNA of all or a portion of the 5' flanking region of the enzyme gene can be used to inhibit expression of the enzyme in vivo. Expression vectors (e.g., retroviral expression vectors) are already available in the art which can be used to generate an antisense RNA of a selected DNA sequence which is expressed in a cell (see, e.g., U.S. Pat. Nos. 4,868,116; 4,980,286). Accordingly, DNA containing all or a portion of the sequence of the 5' flanking region of the enzyme gene can be inserted into an appropriate expression vector so that upon passage into the cell, the transcription of the inserted DNA yields an antisense RNA that is complementary to the mRNA transcript of the enzyme gene normally found in the cell. This antisense RNA transcript of the inserted DNA can then base-pair with the normal mRNA transcript found in the cell and thereby prevent the mRNA from being translated. It is of course necessary to select sequences of the 5' flanking region that are downstream from the transcriptional start sites for the enzyme gene to ensure that the antisense RNA contains complementary sequences present on the mRNA.

Antisense RNA can be generated in vitro also, and then inserted into cells. Oligonucleotides can be synthesized on an automated synthesizer (e.g., Model 8700 automated synthesizer of Milligen-Biosearch, Burlington, Mass. or ABI Model 380B). In addition, antisense deoxyoligonucleotides have been shown to be effective in inhibiting gene transcription and viral replication (see e.g., Zamecnik et al., 1978 *Proc. Natl. Acad. Sci. USA* 75, 280–284; Zamecnik et al., 1986 *Proc. Natl. Acad. Sci. USA,* 83, 4143–4146; Wickstrom et al., 1988 *Proc. Natl. Acad. Sci. USA* 85, 1028–1032; Crooke, 1993 *FASEB J.* 7, 533–539. Inhibition of expression of a gene by antisense oligonucleotides is possible if the antisense oligonucleotides contain modified nucleotides (see, e.g., Offensperger et al., 1993 *EMBO J.* 12, 1257–1262 (in vivo inhibition of duck hepatitis B viral replication and gene expression by antisense phosphorothioate oligodeoxynucleotides); Rosenberg et al., PCT WO 93/01286 (synthesis of sulfurthioate oligonucleotides); Agrawal et al., 1988 *Proc. Natl. Acad. Sci. USA* 85, 7079–7083 (synthesis of antisense oligonucleoside phosphoramidates and phosphorothioates to inhibit replication of human immunodeficiency virus-1); Sarin et al., 1989 *Proc.*

Natl. Acad. Sci. USA 85, 7448–7451 (synthesis of antisense methylphosphonate oligonucleotides); Shaw et al., 1991 Nucleic Acids Res 19, 747–750 (synthesis of 3' exonuclease-resistant oligonucleotides containing 3' terminal phosphoroamidate modifications); incorporated herein by reference).

The sequences of the 5' flanking region of enzyme gene can also be used in triple helix (triplex) gene therapy. Oligonucleotides complementary to gene promoter sequences on one of the strands of the DNA have been shown to bind promoter and regulatory sequences to form local triple nucleic acid helices which block transcription of the gene (see, e.g., 1989 Maher et al., Science 245, 725–730; Orson et al., 1991 Nucl. Acids Res. 19, 3435–3441; Postal et al., 1991 Proc. Natl. Acad. Sci. USA 88, 8227–8231; Cooney et al., 1988 Science 241, 456–459; Young et al., 1991 Proc. Natl. Acad. Sci. USA 88, 10023–10026; Duval-Valentin et al., 1992 Proc. Natl. Acad. Sci. USA 89, 504–5,08; 1992 Blume et al., Nucl. Acids Res. 20, 1777–1784; 1992 Grigoriev et al., J. Biol. Chem. 267, 3389–3395.

Both theoretical calculations and empirical findings have been reported which provide guidance for the design of oligonucleotides for use in oligonucleotide-directed triple helix formation to inhibit gene expression. For example, oligonucleotides should generally be greater than 14 nucleotides in length to ensure target sequence specificity (see, e.g., Maher et al., (1989); Grigoriev et al., (1992)). Also, many cells avidly take up oligonucleotides that are less than 50 nucleotides in length (see e.g., Orson et al., (1991); Holt et al., 1988 Mol. Cell. Biol. 8, 963–973; Wickstrom et al., 1988 Proc. Natl. Acad. Sci. USA 85, 1028–1032). To reduce susceptibility to intracellular degradation, for example by 3' exonucleases, a free amine can be introduced to a 3' terminal hydroxyl group of oligonucleotides without loss of sequence binding specificity (Orson et al., 1991). Furthermore, more stable triplexes are formed if any cytosines that may be present in the oligonucleotide are methylated, and also if an intercalating agent, such as an acridine derivative, is covalently attached to a 5' terminal phosphate (e.g., via a pentamethylene bridge); again without loss of sequence specificity (Maher et al., (1989); Grigoriev et al., (1992)).

Methods to produce or synthesize oligonucleotides are well known in the art. Such methods can range from standard enzymatic digestion followed by nucleotide fragment isolation (see e.g., Sambrook et al., Chapters 5, 6) to purely synthetic methods, for example, by the cyanoethyl phosphoramidite method using a Milligen or Beckman System 1Plus DNA synthesizer (see also, Itakura et al., in Ann. Rev. Biochem. 1984 53, 323–356 (phosphotriester and phosphite-triester methods); Narang et al., in Methods Enzymol., 65, 610–620 (1980) (phosphotriester method). Accordingly, DNA sequences of the 5' flanking region of the enzyme gene described herein can be used to design and construct oligonucleotides including a DNA sequence consisting essentially of at least 15 consecutive nucleotides, with or without base modifications or intercalating agent derivatives, for use in forming triple helices specifically within the 5' flanking region of an enzyme gene in order to inhibit expression of the gene.

In some cases it may be advantageous to insert enhancers or multiple copies of the regulatory sequences into an expression system to facilitate screening of methods and reagents for manipulation of expression.

Preparation of Protein Fragments or Amino Acid Analogs

Compounds which are effective for blocking binding of the transporter or IDO can also consist of protein fragments, expressed recombinantly and cleaved by enzymatic digest or expressed from a sequence encoding a peptide of less than the fall length protein, or trypophan analogs which compete with tryptophan for binding and/or uptake by the high affinity tryptophan transporter. It is a routine matter to make appropriate protein fragments, and test for inhibition of activity of the protein in the presence of the fragments. The preferred fragments are of human origin, in order to minimize potential immunological response. The peptides can be as short as five to eight amino acids in length and are easily prepared by standard techniques. They can also be modified to increase in vivo half-life, by chemical modification of the amino acids or by attachment to a carrier molecule or inert substrate. The peptides can also be conjugated to a carrier protein such as keyhole limpet hemocyanin by its N-terminal cysteine by standard procedures such as the commercial Imject kit from Pierce Chemicals or expressed as a fusion protein, which may have increased efficacy. As noted above, the peptides can be prepared by proteolytic cleavage of the proteins, or, preferably, by synthetic means. These methods are known to those skilled in the art. An example is the solid phase synthesis described by J. Merrifield, 1963 J. Am. Chem. Soc. 85,2149–2154, used in U.S. Pat. No. 4,792,525, and described in U.S. Pat. No. 4,244,946, wherein a protected alpha-amino acid is coupled to a suitable resin, to initiate synthesis of a peptide starting from the C-terminus of the peptide. Other methods of synthesis are described in U.S. Pat. Nos. 4,305,872 and 4,316,891. These methods can be used to synthesize peptides having identical sequence to the proteins described herein, or substitutions or additions of amino acids, which can be screened for activity as described above.

The peptide can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Peptides containing cyclopropyl amino acids, or amino acids derivatized in a similar fashion, can also be used. These peptides retain their original activity but have increased half-lives in vivo. Methods known for modifying amino acids, and their use, are known to those skilled in the art, for example, as described in U.S. Pat. No. 4,629,784 to Stammer.

Pharmaceutical Compositions

Compounds which alter enzyme activity are preferably administered in a pharmaceutically acceptable vehicle. Suitable pharmaceutical vehicles are known to those skilled in the art. For parenteral administration, the compound will usually be dissolved or suspended in sterile water or saline.

Generation of Transgenic Animals for Screening

With the knowledge of the cDNA encoding the high affinity tryptophan transporter and regulatory sequences regulating expression thereof, it is possible to generate transgenic animals, especially rodents, for testing the compounds which can alter enzyme expression, translation or function in a desired manner.

There are basically two types of animals which are useful: those not expressing the high affinity transporter, and those which overexpress the high affinity transporter, either in those tissues which already express the protein or in those tissues where only low levels are naturally expressed. The animals in the first group are preferably made using techniques that result in "knocking out" of the gene for enzyme, although in the preferred case this will be incomplete, either only in certain tissues, or only to a reduced amount. These animals are preferably made using a construct that includes complementary nucleotide sequence to the enzyme gene, but does not encode functional enzyme, and is most preferably used with embryonic stem cells to create chimeras. Animals which are heterozygous for the defective gene can also be obtained by breeding a homozygote normal with an animal which is defective in production of enzyme.

The animals in the second group are preferably made using a construct that includes an unregulated promoter or one which is modified to increase expression as compared with the native promoter. The regulatory sequences for the enzyme gene can be obtained using standard techniques based on screening of an appropriate library with the cDNA encoding enzyme. These animals are most preferably made using standard microinjection techniques.

These manipulations are performed by insertion of cDNA or genomic DNA into the embryo using microinjection or other techniques known to those skilled in the art such as electroporation, as described below. The DNA is selected on the basis of the purpose for which it is intended: to inactivate the gene or to overexpress the gene. The enzyme encoding gene can be modified by homologous recombination with a DNA for a defective enzyme, such as one containing within the coding sequence an antibiotic marker, which can then be used for selection purposes.

Animals suitable for transgenic experiments can be obtained from standard commercial sources. These include animals such as mice and rats for testing of genetic manipulation procedures, as well as larger animals such as pigs, cows, sheep, goats, and other animals that have been genetically engineered using techniques known to those skilled in the art. The procedures for manipulation of the embryo and for microinjection of DNA are described in detail in Hogan et al. Manipulating the mouse embryo, Cold Spring Harbor Laboratory, Cold Spring Harbor, N.Y. (1986), the teachings of which are incorporated herein. These techniques are readily applicable to embryos of other animal species, and, although the success rate is lower, it is considered to be a routine practice to those skilled in this art. Methods for the culturing of ES cells and the subsequent production of transgenic animals, the introduction of DNA into ES cells by a variety of methods such as electroporation, calcium phosphate/DNA precipitation, and direct injection are described in detail in *Teratocarcinomas and embryonic stem cells, a practical approach*, ed. E. J. Robertson, (IRL Press 1987), the teachings of which are incorporated herein. Transfection is carried out by one of several methods described in detail in Lovell-Badge, in *Teratocarcinomas and embryonic stem cells, a practical approach*, ed. E. J. Robertson, (IRL Press 1987) or in Potter et al. *Proc. Natl. Acad. Sci. USA* 81, 7161–7165 (1984). Calcium phosphate/DNA precipitation, direct injection, and electroporation are the preferred methods. DNA molecules introduced into ES cells can also be integrated into the chromosome through the process of homologous recombination, described by Capecchi, (1989). Direct injection results in a high efficiency of integration. Desired clones are identified through PCR of DNA prepared from pools of injected ES cells. Positive cells within the pools are identified by PCR subsequent to cell cloning (Zimmer and Gruss, *Nature* 338, 150–153 (1989)).

Once the transgenic animals are identified, lines are established by conventional breeding and used as the donors for tissue removal and implantation using standard techniques for implantation into humans.

Gene Therapy

Altered levels of transporter can also be achieved using gene therapy, either to administer nucleotide molecules which inhibit transporter activity, or to increase transporter activity either through direct alteration of activity, for example by increasing substrate binding affinity, or through overexpression.

EXAMPLES

The following methods and materials were used in the examples.

Materials. Recombinant human macrophage colony-stimulating factor (MCSF) was the gift of Genetics Institute, Cambridge Mass. Recombinant human interferon-γ (IFNγ) was the gift of Genentech, South San Francisco, Calif. Radiolabeled [$^3$H]tryptophan (21 Ci/mmol) was obtained from Amersham USA. All preparations were adjusted with their respective unlabeled amino acids to a specific activity of 20 Ci/mmol before use. Unlabeled amino acids and all other reagents were obtained from Sigma unless otherwise specified. Tyrosine and other sparingly-soluble amino acids were dissolved in 0.1 M NaOH prior to dilution.

Monocyte isolation and culture. Human peripheral blood monocytes were isolated from healthy volunteer donors by leukocytapheresis and counterflow centrifugal elutriation, following appropriate informed consent under a protocol approved by our Institutional Review Board. Monocytes of greater than 95% purity by cell surface markers (Munn and Armstrong 1993 Cancer Res. 53, 2603–2613) were cultured as described by Munn and Cheung 1989 *J. Exp. Med.* 170, 511–526, for 7 days in the presence of MCSF (200 U/ml). The monocytic leukemia lines THP-1 and U-937 were obtained from the American Type Culture Collection, Rockville, Md.

Uptake measurements. Single cell suspensions were obtained by treating macrophage monolayers with 2 mM EDTA in Hanks balanced salt solution for 15 minutes at room temperature. Cells were washed twice in Tris-choline buffer (150 mM choline chloride, 10 mM tris, pH 7.4), suspended in Tris-choline at between one and $2 \times 10^6$ cells/ml, and 100 μl/well added to 96 well microtiter plates. Titrations of radiolabeled amino acids were then transferred to the assay plate and uptake allowed to proceed for 10 minutes (the linear range). At the end of the assay period, wells were harvested simultaneously onto glass-fiber filters and washed vigorously for 30 seconds with phosphate buffered saline solution using a Tomtec 96 well parallel harvester. Nonspecific binding of radioactivity to the filters (based on wells without cells) was typically less than 10% of the total signal, and was subtracted from each data point. All assays were performed in triplicate; where error bars are not shown the SD between replicates was less than 10%. In all assays, the uptake rate (V) was normalized per $1 \times 10^6$ cells (expressed as pmol $10^6$ cells$^{-1}$ 10 min$^{-1}$). Normalization to milligrams protein was considered less informative because protein content can change markedly during macrophage differentiation, independently of other functional attributes.

Analysis of saturation kinetics. Uptake kinetics were analyzed using an Eadie-Hofstee transformation (V/[S] vs.

V) to identify linear concentration ranges for each transporter. Data from these two ranges were then analyzed separately using double-reciprocal (Lineweaver-Burk, 1/[S] vs. 1/V) plots to determine Km and Vmax. In all cases, comparable results were obtained if these parameters were estimated from the Eadie-Hofstee plots. Regression analysis was performed using the Microsoft Excel spreadsheet program. Kinetic parameters were calculated on a minimum of 4–6 points, and were considered reliable if the correlation coefficient of the regression line was greater than 0.95.

For competitive inhibition studies, the Ki value for each competitor was estimated by fitting the measured inhibition curve to the formula in Equation 1 (Cheng and Prusoff 1973, *Biochem. Pharmacol.* 22, 3099–3108).

EQUATION 1:

$$Vi = \frac{Vmax \cdot [S]}{Km \cdot \left(1 + \frac{[I]}{Ki}\right) + [S]}$$

where [S] is the concentration of labeled substrate, [I] is the concentration of unlabeled inhibitor, Vi is the observed rate of uptake in the presence of inhibitor, Ki is the putative affinity constant of the inhibitor for the transporter, and Km and Vmax have their customary meanings. This equation assumes a single transport system and so does not fully model the situation in macrophages, where two transporters are present. However, the affinity constants of the two systems differed so widely (100-fold) that the data closely fit a single-system model at substrate concentrations surrounding the respective Km values.

Example 1

Tryptophan Transport is Sodium-independent and Occurs Via Two Transport Systems

Monocyte derived macrophages were incubated with radiolabeled tryptophan (125 nM) for 2, 4, 6 or 10 minutes, either in buffered saline solution (150 mM NaCl) or buffered choline chloride. The majority of tryptophan uptake is sodium-independent. Uptake in the absence of sodium was 86±6% of uptake in saline, n=4 Therefore all subsequent assays were performed in the absence of sodium.

Saturation kinetics at low substrate concentrations (less than 2.5 $\mu$M) indicated that the tryptophan transport system is a saturable system with very high affinity (FIG. 1A). Studies over an extended range of concentrations revealed that tryptophan uptake did not follow simple Michaelis-Menten kinetics. Analyzing the data with Eadie-Hofstee (V/[s] vs. V) plots suggested the presence of two transport system, as indicated by the non-linear nature of the transformed data (FIG. 1B). The transport kinetics were analyzed separately at high (8–64 $\mu$M) and low (less than 1 $\mu$M) substrate concentrations, using Lineweaver-Burk plots (FIG. 1C). Individually the data indicated two independent, saturable transport systems, the first with a low affinity (Km of 20–30 $\mu$M, which is in the usual range for previously described "high-affinity" amino acid transporters (Sanchez del Pino, et al., 1995, *J. Biol. Chem.* 270, 14913–14918; Mokrzan, et al., 1995, *J. Pharmacol. Exp. Ther.* 272, 1277–1284; Low, et al., 1993, *J. Cell Physiol.* 156, 626–634; Prasad, et al., 1994, *Endocrinol.* 134, 574–581; and Low, et al., 1994, *J. Biol. Chem.* 269, 32098–32103)), and the second system with a very high affinity (Km of approximately 300 nM). When the Km and Vmax constants obtained from these separate analyses were employed with the Michaelis-Menten equation to generate Theoretical predicated uptake curves for each system were generated, using the Km and Vmax values derived from the independent analysis of the low affinity data set and the high affinity data set. The observed data over the range of concentrations surrounding each Km fit well to the generated curves (the predicted regression lines are superimposed on FIG. 1B). Therefore, tryptophan uptake in macrophages was modeled best as two independent transport systems, each following classical Michaelis-Menton kinetics but with markedly different affinities for the substrate.

Table I summarizes the high-affinity system in human macrophages and two human macrophage-like cell lines, THP-1 and U-937. Human macrophages were allowed to differentiate for seven days under the influence of macrophage colony stimulating factor (MCSF). Macrophages and cell lines were assayed for tryptophan uptake, and the Km value was determined for the range of substrate concentrations 32 nM–1 $\mu$M.

TABLE 1

Presence of the high-affinity tryptophan transporter in macrophages and macrophage-like cell lines.

| Cell type | Km ($\mu$M) | Experiments (n) |
| --- | --- | --- |
| macrophages | 0.29 ± 0.16 | 18 |
| THP-1 | 0.25 ± 0.12 | 11 |
| U-937 | 0.34 ± 0.33 | 3 |

Example 2

Uptake Via the Lower-affinity System is Consistent with System L

Of the known sodium-independent transport systems only system L accepts tryptophan with low-micromolar affinity (reported affinity as high as Km=8–30 $\mu$M). This was consistent with the values observed for the lower-affinity system (Km=27±4 $\mu$M, n=4, FIG. 1) herein described. Leucine and phenylalanine, as shown in FIGS. 2a,b,c, which are both known substrates for system L, were transported via the low affinity system with comparable affinity. Tryptophan competed with phenylalanine for uptake via this system, with a Ki value similar to the Km value for its own uptake via the lower-affinity system (FIGS. 1B and 1C). Cross-competition experiments showed that tryptophan transport could be at least partially inhibited by a number of other neutral amino acids, which is also consistent with a contribution of system L in tryptophan transport.

BCH is a substrate which is used as the model substrate for system L transport. FIG. 3 indicates that tryptophan transport is inhibited by CH, but not by charged amino acids. Thus, the lower-affinity transport system present in macrophages displayed multiple features consistent with system L, and is very likely system L or a new transport system with characteristics much like those of system L.

Example 3

Uptake Via the High-affinity System is Distinct from System L and Very Specific for Tryptophan Uptake via system L was distinguished from uptake via the previously unidentified high-affinity system. BCH was used to selectively compete for uptake via system L. As shown in FIG. 4A, the $IC_{50}$ for inhibition of tryptophan transport by BCH was approximately 100-fold greater than the $IC_{50}$ for inhibition by tryptophan itself. Using Equation 1, the data for BCH fit well to a single system, competitive-inhibition model with a Ki equal to the observed $IC_{50}$ of 37 μM. In contrast, inhibition by unlabeled tryptophan fit to a much higher affinity model (Ki=$IC_{50}$=360 nM in the experiment shown), and BCH showed no evidence of competition for this system (as indicated by the lack of inhibition at competitor concentrations less than 1 μM).

The saturation kinetics of tryptophan transport were compared in the presence or absence of BCH. BCH was found to act as a competitive inhibitor over the range of substrate concentrations affected by system L, but it interacted only weakly ($IC_{50}$>500 μM) with the high-affinity system (FIG. 4C). More importantly, the interaction between BCH and the high affinity system was strictly non-competitive. BCH did not compete with tryptophan for transport via the high-affinity system. Similar results were obtained for leucine and phenylalanine, indicating that leucine and phenylalanine do not compete with tryptophan for transport by the high affinity system. Thus, while tryptophan competed with multiple substrates for transport by system L, the high-affinity component of tryptophan transport is selective for tryptophan.

Figure 2B:
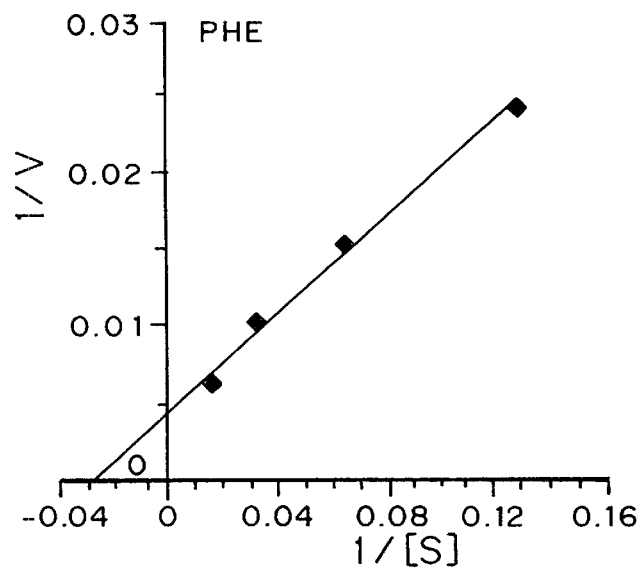
Figure 2C:
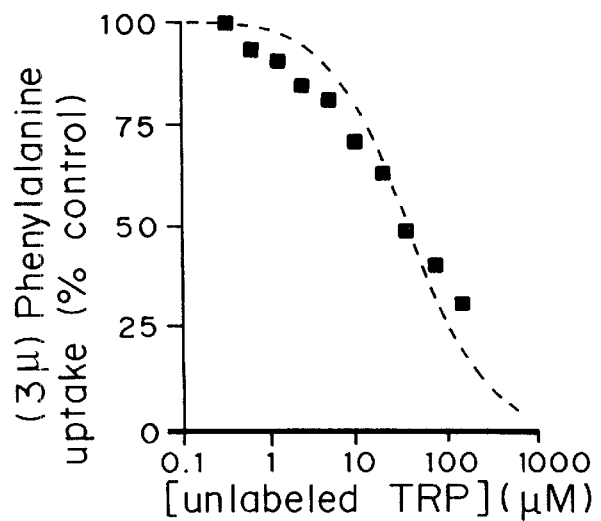
FIG. 2C is a saturation graph of tryptophan competition with phenylalanine for uptake. The dotted line shows the predicted inhibition curve calculated from Equation 1 based on the observed $IC_{50}$ for the low affinity system L.

The data represented in FIG. 2 indicated that even at 8000 μM competitor, tryptophan was not fully inhibited from being transported. Since tryptophan competed with these other substrates at approximately 30 μM (FIGS. 2 and 4), then a single system composed of system L under these conditions would have less than 1% of the tryptophan being transported. Since there are two transport systems either the transport systems have the same specificity or different. If the high affinity transport system had specificity requirements similar to system L, then 8000 μM competitor should have reduced tryptophan transport to below 1% of the control, as if there was only one system. Therefore, this data (FIGS. 2, 3, 4) also indicated that the transport of tryptophan is occurring via different pathways, one of which is highly specific for tryptophan, relative to other amino acids.

Figure 5:
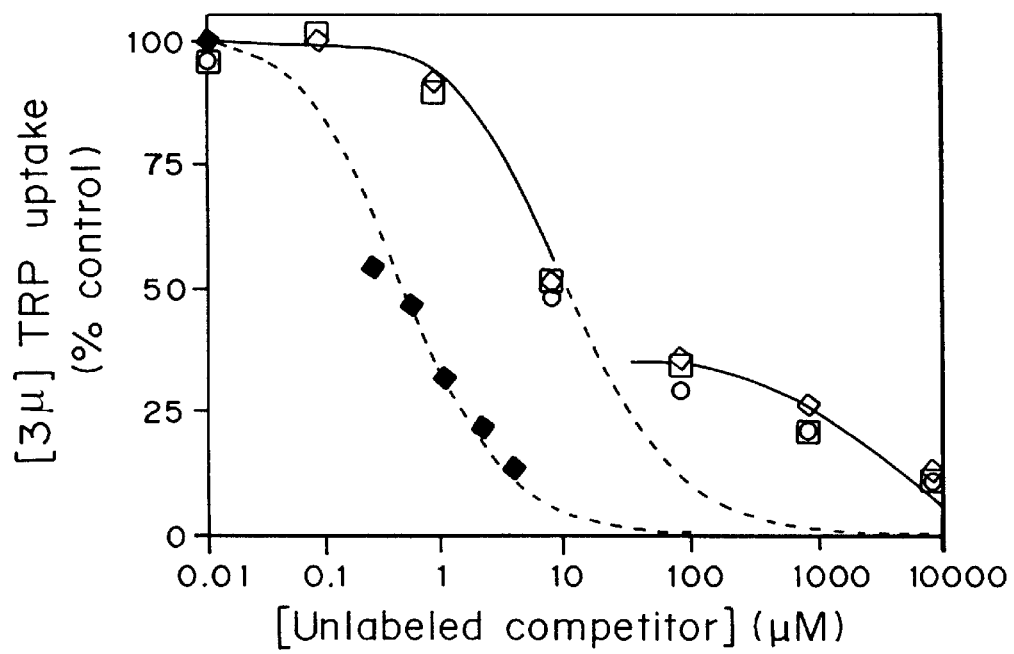
FIG. 5 is a graph of $^3$H]Tryptophan (%control) versus [unlabeled competitor] ($\mu$M). Unlabeled phenylalanine (open symbols) was allowed to compete for uptake with radiolabeled tryptophan (125 nM). Equation 1 was used to calculate the predicted inhibition curves (dotted lines) assuming that labeled and unlabeled substrate competed for a single system, with Ki in each case equal to the observed $IC_{50}$. This model correctly predicted the behavior of unlabeled tryptophan competing for its own uptake (competition for the high-affinity system, solid diamonds), and of phenylalanine at low concentrations (competition for system L, open symbols). However, at high concentrations of phenylalanine the observed data departed significantly from that predicted for a single system. Each of the 3 open symbols show data from separate experiments. A total of 11 experiments were performed using phenylalanine, leucine, tyrosine, or cysteine as competitors, all with similar departure from the predicted single-system kinetics.

Extended totrations were performed using several unlabeled competitors (leucine, phenylalanine, tyrosine, cysteine, and BCH) (FIG. 3). Phenylalanine was identified as the most effeicient competitor, and data for this representative substrate are shown in FIG. 5. Like BCH, phenylalanine displayed no detectable competition for the high-affinity system (i.e., no inhibition at competitor concentrations less than 1 μM). Based on the $IC_{50}$, phenylalanine was predicted to compete with tryptophan with a Ki of approximately 10 μM. howvere, at high competitor concentrations the abserved inhibition departed markedly from that predicted for a single system. instead, tryptophan uptake continued at a rate significantly higher than expected, suggesting the presence of an additional transporter not subject to competition by phenylalanine. Titrations of leucine, tyrosine, cysteine, and BCH all showed similar patterns, with even less interaction with the tryptophan-selective component, which was consistent with the results shown in FIG. 3.

Figure 6:
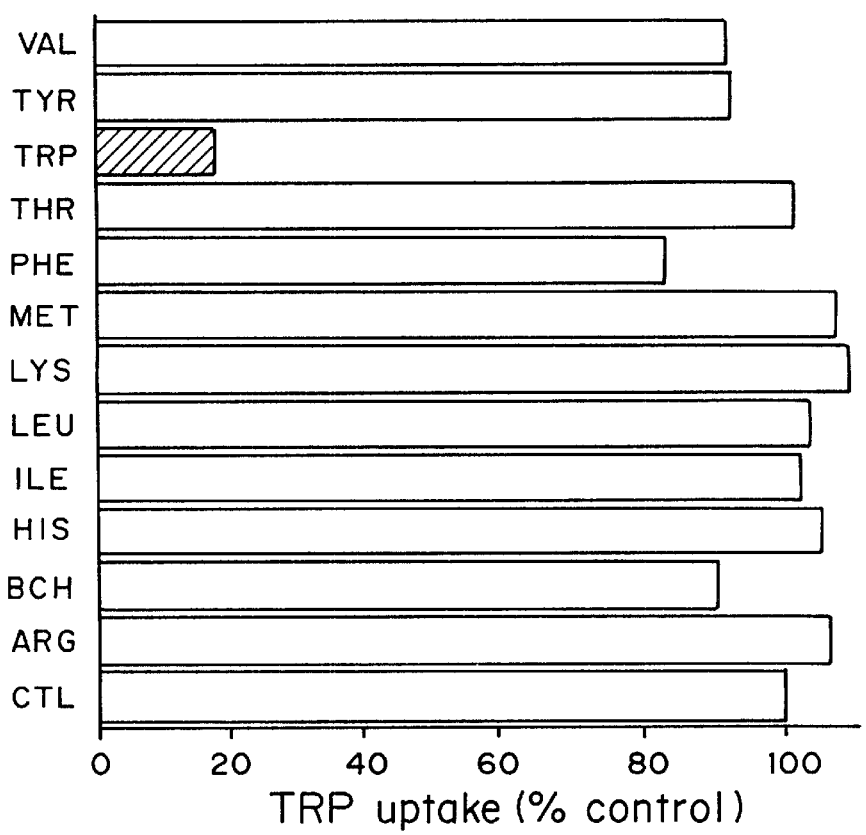
FIG. 6 is a bar graph of the amount of uptake of different amino acids based on the % of tryptophan uptake. Cross-competition studies were performed as described for FIG. 3, but using a concentration of unlabeled competitor (4 $\mu$M) predicted to affect only the high-affinity system.

The cross-competition studies shown in FIG. 3 were repeated using unlabeled competitors at a concentration of 4 μM rather than 8000 μM. Based on Equation 1, this concentration was predicted to significantly inhibit the higher-affinity system (80% inhibition) but have little impact (less than 10% inhibition) on the lower-affinity system. As shown in FIG. 6, tryptophan uptake was markedly inhibited by 4 μM unlabeled tryptophan, but BCH and all other substrates tested had minimal effect. Thus, when tested in isolation, the high-affinity system displayed a pattern of substrate specificity entirely different from that of system L or any of the known sodium-independent transport systems, and appeared highly selective for tryptophan.

Example 4

Tryptophan Does Not Compete with Other Substrates for the High-affinity System

The data presented in Examples 1–3 is not consistent with a single system that has markedly higher affinity for tryptophan because tryptophan was not able to preferentially compete for uptake over other substrates. An additional study in which unlabeled tryptophan was allowed to compete for uptake of radiolabeled leucine, phenylalanine, or tryptophan, all at 125 nM shows that tryptophan competed with labeled leucine or phenylalanine only for the shared system L, and only with the expected affinity (Ki+30 μM). There was no detectable high-affinity inhibition of phenylalanine or leucine uptake by tryptophan. In contrast, tryptophan competed for its own uptake with the predicted high affinity. Therefore, the data supported the existence of two separate transporters, with the high-affinity system being selective for tryptophan.

Figure 7:
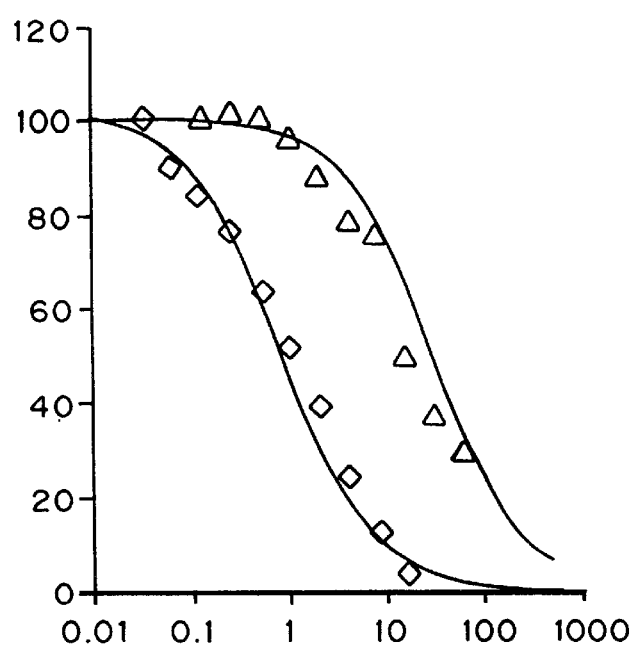
FIG. 7 is a graph of percent labeled tryptophan (250 nM radiolabelled tryptophan) taken up by the high affinity transporter as a function of concentration of either unlabelled tryptophan (diamonds) or unlabeled 1-methyl tryptophan (triangles) of different concentrations. The solid line through the diamonds shows the predicted inhibition curve if tryptophan competed with a Ki equal to the measured Km of the high affinity system (290 nM). The solid line through the triangles shows the predicted inhibition curve if 1-methyl tryptophan competed with a Ki of 30 $\mu$M, the measured Km of system L.

No other amino acid transporter accepting tryptophan has the same very high degree of specificity. As shown by FIG. 7, comparing the amount of labeled tryptophan (250 nM radiolabelled tryptophan) taken up by the high affinity transporter as a function of concentration of either unlabelled tryptophan or unlabeled 1-methyl tryptophan at different concentrations. The solid line through the diamonds shows the predicted inhibition curve if tryptophan competed with a Ki equal to the measured Km of the high affinity system (290 nM). The solid line through the triangles shows the predicted inhibition curve if 1-methyl tryptophan competed with a Ki of 30 μM, the measured Km of system L. There was no competition by 1-methyl tryptophan for the high affinity system.

The same type of experiment was done with D-tryptophan, serotonin, 5-hydroxy tryptophan and N-acetyl tryptophan. These additional substrates also did not compete with tryptophan for the high-affinity system.

Example 5

High-affinity Tryptophan Uptake Reflects Transmembrane Transport

To distinguish between transmembrane transport and binding of tryptophan to a high-affinity cell-surface receptor, the uptake of tryptophan at 25° C. and 0° C. was compared. As shown in FIG. 8, the rate of tryptophan accumulation was reduced by 90% at 0° C., and this difference remained constant over an extended assay period (30 min). Thus, the accumulation of cell-associated tryptophan was consistent with transmembrane transport rather than surface-receptor binding.

Example 6

The High-affinity System is Induced During Macrophage Differentiation

Figure 9A:
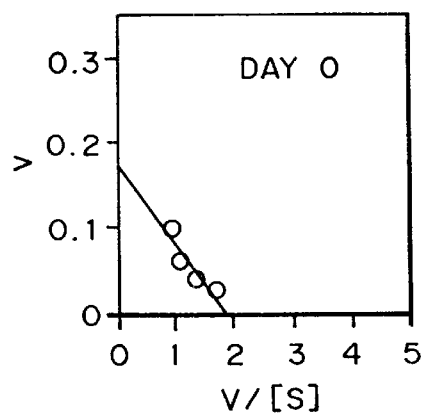
FIGS. 9A and 9B are graphs of V versus V/[S] Peripheral blood monocytes were allowed to differentiate in vitro for up to 7 days under the influence of MCSF. Saturation kinetics for tryptophan uptake were performed as in FIG. 1, over the range of 0.032 –1 $\mu$M substrate.
Figure 9B:
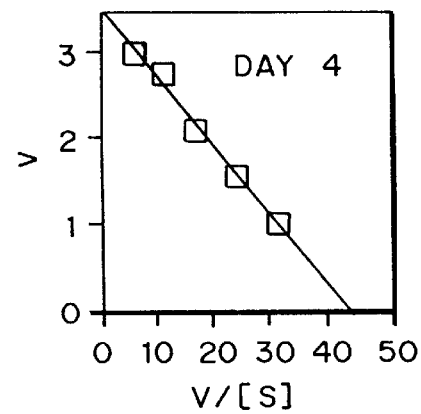
Figure 9C:
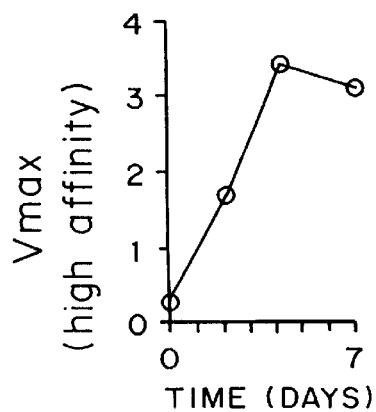
FIG. 9C is a graph of Vmax (high affinity transporter) versus Time (days). This graph illustrates the upregulation that takes place during macrophage differentiation.

Peripheral blood monocytes undergo many functional changes as they differentiate into macrophages. The high-affinity tryptophan transporter was regulated during macrophage differentiation. For these experiments, transporter expression was defined as the Vmax for the high affinity component derived from Eadie-Hofstee plots (FIG. 2). As shown in FIGS. 9a,b,c, the high affinity system underwent a 10–30 fold upregulation in Vmax during macrophage differentiation. By comparison, the system L component underwent only a 2- to 3-fold induction over the same period (from 14±8 to 27±4 pmol $10^6$ cells$^{-1 \cdot}$ 10 min$^{-1}$, n=4). Thus, the high-affinity system was markedly and selectively induced during macrophage differentiation.

What is claimed is:

1. An isolated and purified high affinity transporter protein for tryptophan having a Km of between approximately 130 nM and approximately 450 nM, which exhibits preferential uptake of tryptophan relative to the amino acids selected from the group of VAL, TYR, THR, PHE, MET, LYS, LEU, IlE, HIS, BCH, and ARG when measured at the Km value of the high affinity transporter protein, and which is inducible during macrophage differentation.

2. The transporter protein of claim 1 wherein the protein is isolated from human monocyte-derived macrophages.

3. The transporter protein of claim 1 which is expressed in fresh monocytes and undergoes a 10 fold to 30 fold induction during macrophage differentiation.

4. The transporter protein of claim 1 wherein the Km value is within a range of 290 nM to 340 nM.

5. An isolated and purified high affinity transporter protein for tryptophan having a Km of between approximately 130 nM and approximately 450 nM, which exhibits preferential uptake of tryptophan relative to the amino acids selected from the group of VAL, TYR, THR, PHE, MET, LYS, LEU, ILE, HIS, BCH, and ARG when measured at the Km value of the high affinity transporter protein, which is expressed in fresh monocytes and undergoes a 10 fold to 30 fold induction during macrophage differentiation, and wherein the protein is isolated from human monocyte-derived macrophages.

6. An isolated and purified high affinity transporter protein for tryptophan having a Km value is within a range of 290 nM to 340 nM, which exhibits preferential uptake of tryptophan relative to the amino acids selected from the group of VAL, TYR, THR, PHE, MET, LYS, LEU, ILE, HIS, BCH, and ARG when measured at the Km value of the high affinity transporter protein, which is inducible during macrophage differentiation, and wherein the protein is isolated from human monocyte-derived macrophages.

7. An isolated and purified high affinity transporter protein for tryptophan having a Km value is within a range of 290 nM to 340 nM, which exhibits preferential uptake of tryptophan relative to the amino acids selected from the group of VAL, TYR, THR, PHE, MET, LYS, LEU, ILE, HIS, BCH, and ARG when measured at the Km value of the high affinity transporter protein, which is expressed in fresh monocytes and undergoes a 10 fold to 30 fold induction during macrophage differentiation.

* * * * *

UNITED STATES PATENT AND TRADEMARK OFFICE
CERTIFICATE OF CORRECTION

PATENT NO.    : 6,395,876 B1
DATED         : May 28, 2002
INVENTOR(S)   : David Munn and Andrew Mellor It is certified that error appears in the above-identified patent and that said Letters Patent is hereby corrected as shown below:

<u>Column 19,</u>
Line 15, delete "IIE," and insert -- ILE, --

Signed and Sealed this

Fourteenth Day of January, 2003

JAMES E. ROGAN
*Director of the United States Patent and Trademark Office*